United States Patent
Kado

[19]
[11] Patent Number: 5,880,588
[45] Date of Patent: Mar. 9, 1999

[54] MAGNETIC MEASURING APPARATUS WITH SENSOR GUIDE DEVICE AND METHOD FOR INSTALLING SENSORS THEREIN

[75] Inventor: Hisashi Kado, Kashiwa, Japan

[73] Assignee: Kanazawa Institute of Technology, Ishikawa, Japan

[21] Appl. No.: 812,304

[22] Filed: Mar. 5, 1997

[30] Foreign Application Priority Data

May 23, 1996 [JP] Japan .................................. 8-128459

[51] Int. Cl.$^6$ ............................ G01R 33/035; A61B 5/05
[52] U.S. Cl. ......................... 324/248; 505/846; 600/409
[58] Field of Search ............................ 324/248; 600/409, 600/415; 505/162, 845, 846

[56] References Cited

U.S. PATENT DOCUMENTS

| | | | |
|---|---|---|---|
| 4,700,135 | 10/1987 | Hoeing . | |
| 5,158,932 | 10/1992 | Hinshaw et al. ................... | 324/248 X |
| 5,309,095 | 5/1994 | Ahonen et al. ................... | 600/409 X |
| 5,442,289 | 8/1995 | DiIorio et al. ..................... | 324/248 |
| 5,471,985 | 12/1995 | Warden . | |
| 5,475,306 | 12/1995 | Ludeke et al. . | |
| 5,490,513 | 2/1996 | Damadian et al. ................. | 600/415 |
| 5,494,033 | 2/1996 | Buchanan et al. ................. | 600/409 |
| 5,713,354 | 2/1998 | Warden ................................. | 600/409 |

FOREIGN PATENT DOCUMENTS

| | | |
|---|---|---|
| 04 92 262A2 | 6/1992 | European Pat. Off. . |
| 2-78983 | 3/1990 | Japan ..................................... 324/248 |
| 4315075 | 11/1992 | Japan . |

OTHER PUBLICATIONS

H. Kado et al, "Multi–Channel SQUID", IEICE Transaction on Electronics, E78–C, 511–518, issued May 1995.

M. Ueda et al, "Development of a biomagnetic measurement system for brain research", IEEE Trans. On Applied Superconductivity, 5, 2465–2469, issued on Jun. 1995.

K. Tsukada et al, "Multichannel SQUID system detecting tangential components of the cardiac field", Review od Scientific Instruments, 66, 5085–5091, issued Oct. 1995.

*Primary Examiner*—Gerard Strecker
*Attorney, Agent, or Firm*—Jordan and Hamburg LLP

[57] ABSTRACT

Apparatus for measuring weak magnetic fields includes a cryogenic vessel CR having a domed bottom D for accepting a human head, a plurality of magnetic sensor units 10 mounted upright on the inner surface of the bottom D of the cryogenic vessel CR, an interface device 20 for receiving output signals of the magnetic sensor units 10 through respective lead lines 4, a data processor device 30 for analyzing the output signals of the magnetic sensor units 10 to specify magnetic fields spread in the ambient space about the human head and calculating the activity of a brain B from the magnetic fields, and a display device 40 for displaying the brain activity. Each of the magnetic sensor units 10 is fed along its guide line G through a small opening OP of the cryogenic vessel CR and mounted upright on the bottom D. As the opening OP of the cryogenic vessel CR is relatively small, the evaporation loss of a coolant in the cryogenic vessel CR is minimized and the running cost of the apparatus will be decreased.

41 Claims, 18 Drawing Sheets

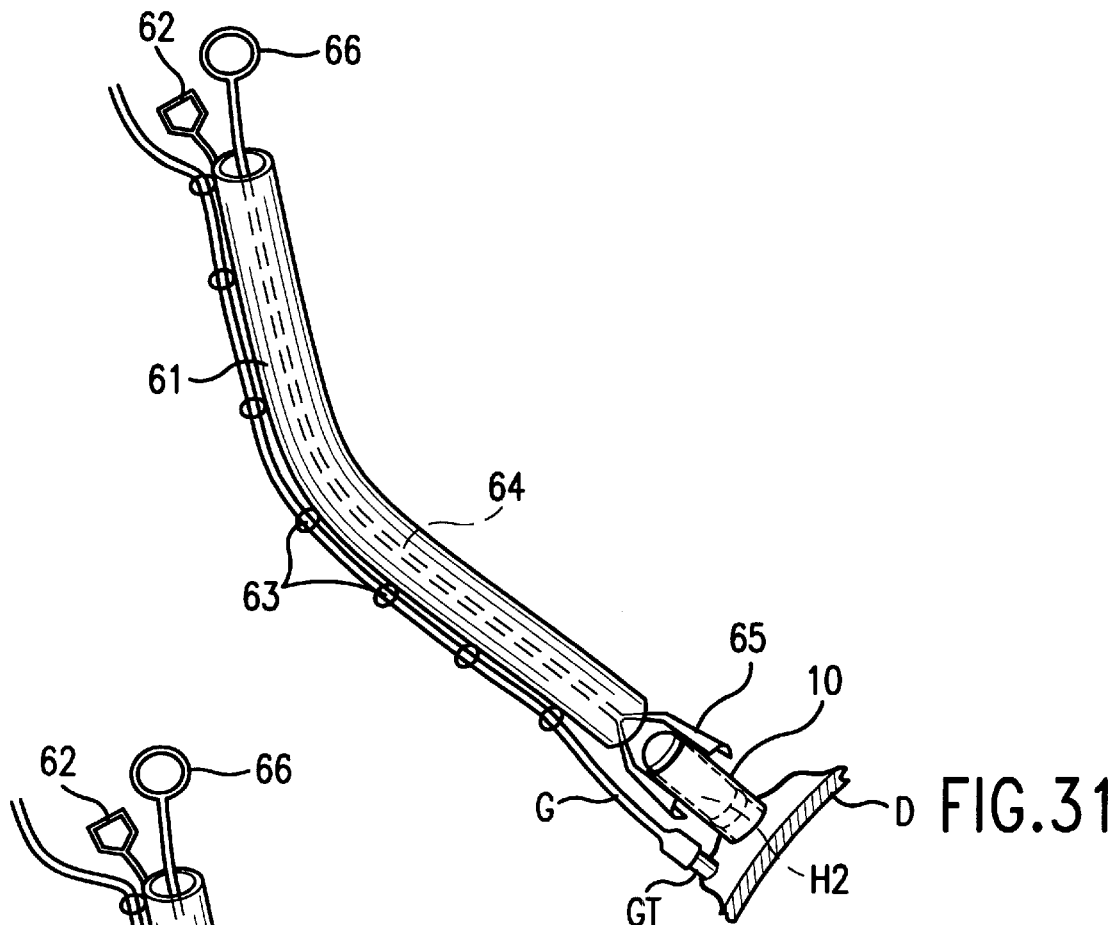
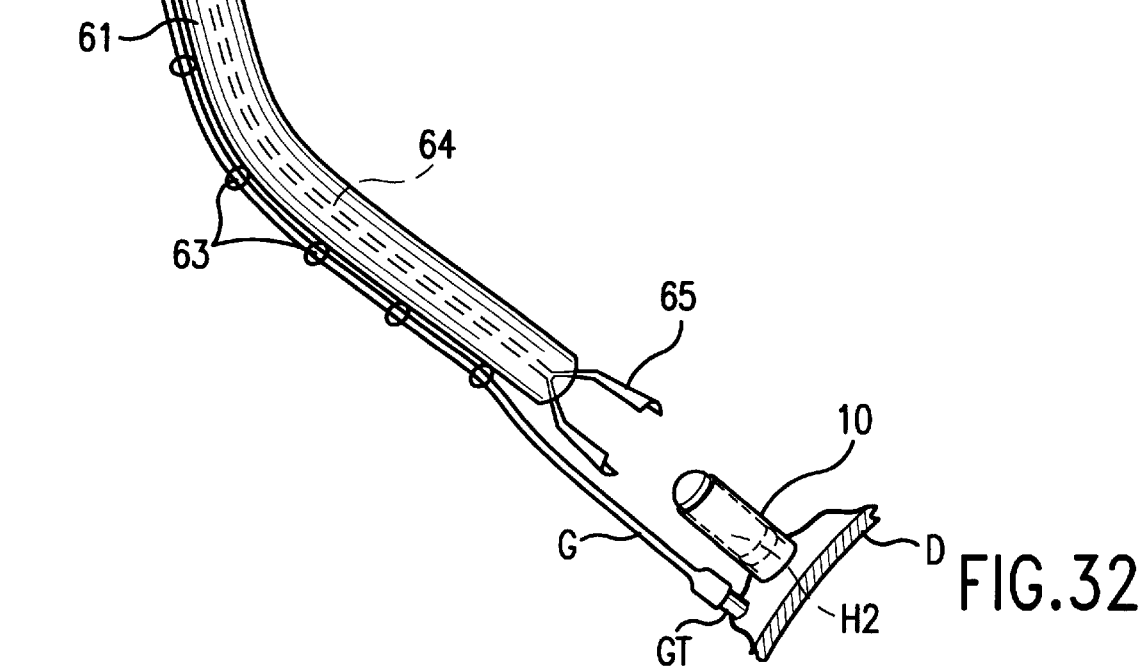

MAGNETIC MEASURING APPARATUS WITH SENSOR GUIDE DEVICE AND METHOD FOR INSTALLING SENSORS THEREIN

BACKGROUND OF THE INVENTION

The present invention relates to a magnetic measuring apparatus and more specifically, to a magnetic measuring apparatus appropriate for measuring magnetic fields spread in an ambient space about a head (brain), a chest (heart, stomach), an abdomen (liver), a fetus, and so on.

FIG. 33 shows a prior art (U.S. Pat. No. 5,475,306) magnetic measuring apparatus for measuring magnetic fields spread in the ambient space about a human bead.

The magnetic measuring apparatus 500 comprises a cryogenic vessel CR' composed of an inner vessel CRI' and an outer vessel CRO having a domed bottom D for accepting the human head, a lid LD' for closing an opening OP' provided in the top of the cryogenic vessel CR', a multiplicity of magnetic sensor units 50 suspended by pipes PP respectively from the lid LD' so as to be seated directly on the upper surface of the domed bottom D, signal lines 4 for transmission of output signals from their respective magnetic sensor units 50, an interface device 20 connected to the signal lines 4, a data processor device 30 for analyzing the output signals of the magnetic sensor units 50 to specify magnetic fields spread in the ambient space about the head and calculating activity data of a brain B from the magnetic fields, and a display device 40 for displaying the calculated activity data.

The space between the inner vessel CSI' and the outer vessel CRO is filled with a thermal insulating material Dn and air is evacuated therefrom.

Denoted by PA is a packing made of e.g. rubber.

A coolant feed/exhaust double tube ST is provided for feeding to and exhausting a coolant from the cryogenic vessel CR'. The coolant may be a liquid helium (4.2K).

As the prior art magnetic measuring apparatus 500 shown in FIG. 33 has the magnetic sensor units 50 mounted in a suspended arrangement, the opening OP' is formed substantially equal in size to the cross section of a human head.

But when the opening OP' is considerably large (over 10 cm in diameter), it causes a problem of passing of much heat thus increasing the evaporation loss of the coolant and the cost of running.

In addition, there is another problem that the cryogenic vessel CR' cannot have an overhand reducing the opening OP' because the magnetic sensor units 50 are vertically suspended from the lid LD'.

Furthermore, there is the other problem that the domed bottom D of the magnetic measuring apparatus 500 accepts the head of one single test object at a time, thus throughput cannot be increased.

SUMMARY OF THE INVENTION

It is a primary object of the present invention to provide a magnetic measuring apparatus which can reduce the evaporation loss of a coolant and allows a cryogenic vessel to have an overhang configuration where the magnetic sensors are mounted beneath the overhang.

It is a secondary object of the present invention to provide a magnetic measuring apparatus capable of accepting a plurality of test objects at a time and increasing the throughput.

For embodying a first feature of the present invention, a measuring apparatus having a plurality of magnetic sensors installed in a cryogenic vessel, signal lines of the magnetic sensors arranged extending out from an opening provided in the top of the cryogenic vessel, a coolant filled in the cryogenic vessel, and a lid closing the opening is provided comprising magnetic sensor holders mounted on a bottom or side of the cryogenic vessel for accepting and holding their respective magnetic sensors, and guide lines joined at a first end to the magnetic sensor holders respectively or their proximities and having a second end extending out from the opening of the cryogenic vessel so that the magnetic sensor is fed and moved from the opening to the corresponding magnetic sensor holder along the guide line.

The bottom or side of the cryogenic vessel may be flat shaped but is preferably formed to an arcuate configuration for matching the shape of a test object. More specifically, the arcuate configuration is a helmet-like shape for accepting a human head or a body-like shape for a human body.

The magnetic measuring apparatus according to the first feature of the present invention permits the magnetic sensors to be fed and moved along their respective guide lines from the opening to the corresponding magnetic sensor holders for installation on the bottom or side of the cryogenic vessel. Hence, the opening of the cryogenic vessel is minimized in size (having a diameter of less than 5 cm) to pass one magnetic sensor together with the signal lines and the evaporation loss of the coolant will significantly be decreased. Also, it is possible to form an undercut portion beneath an overhand of the cryogenic vessel where the magnetic sensors are installed without difficulty.

For embodying a second feature of the present invention, a magnetic measuring apparatus having a plurality of magnetic sensors installed in a cryogenic vessel, signal lines of the magnetic sensors arranged extending out from an opening provided in the top of the cryogenic vessel, a coolant filled in the cryogenic vessel, and a lid closing the opening is provided comprising magnetic sensor holders mounted on a bottom or side of the cryogenic vessel for accepting and holding their respective magnetic sensors, and guide lines joined at first end to the magnetic sensor holders respectively or their proximities and having a second end extending out or enabled to be withdrawn from the opening of the cryogenic vessel so that the magnetic sensor is fed and moved from the opening to the corresponding magnetic sensor holder along the guide line and withdrawn from the corresponding magnetic sensor holder to the opening along the same.

Similarly, the magnetic measuring apparatus according to the second feature of the present invention permits the magnetic sensors to be fed and moved along their respective guide lines from the opening to the corresponding magnetic sensor holders for installation on the bottom or side of the cryogenic vessel. Hence, the opening of the cryogenic vessel is minimized in size (having a diameter of less than 5 cm) to pass one magnetic sensor together with the signal lines and the evaporation loss of the coolant will significantly be decreased. Also, it is possible to form an undercut portion beneath an overhang of the cryogenic vessel where the magnetic sensors are installed without difficulty.

In addition, any of the magnetic sensors can be withdrawn from the opening along the corresponding guide line which has been pulled out with its second end. As the result, replacement or repair of the magnetic sensors will be carried out with much ease.

For embodying a third feature of the present invention, a magnetic measuring apparatus of the prescribed type is provided in which the magnetic sensor is integrated with a pipe body having a through hole through which the guide line is passed.

The magnetic measuring apparatus according to the third feature of the present invention allows the magnetic sensor to be fed and moved from the opening to the corresponding magnetic sensor holder along the guide line which passes through the through hole of the pipe body of the magnetic sensor. This will facilitate the installation of the magnetic sensors on the domed or arcuate region of the cryogenic vessel and even on an undercut portion formed beneath an overhang defining the opening.

For embodying a fourth feature of the present invention, a magnetic measuring apparatus of the prescribed type is provided in which the magnetic sensor holder comprises a support base secured to the bottom or side of the cryogenic vessel for holding the corresponding magnetic sensor as fitted into the through hole of the pipe body, and a flexible guide member extending from the support base.

The magnetic measuring apparatus according to the fourth feature of the present invention allows the pipe body of each magnetic sensor to be fed along the flexible guide member without jerky movement and fitted onto the magnetic sensor support securely. As their pipe bodies are smoothly moved to the corresponding magnetic sensor supports, the magnetic sensors are accurately located on the bottom or side of the cryogenic vessel and even on an undercut portion of an overhang defining the opening.

For embodying a fifth feature of the present invention, a magnetic measuring apparatus of the prescribed type is provided in which the support base of the magnetic sensor holder comprises a first support base secured to the bottom or side of the cryogenic vessel and a second support base pivotably mounted to the first support base.

The magnetic measuring apparatus according to the fifth feature of the present invention permits the second support base to be pivoted on the first support base. Hence, the pipe body of the magnetic sensor is readily fitted onto the support base without jerky movement.

For embodying a sixth feature of the present invention, a magnetic measuring apparatus of the prescribed type is provided in which the guide line is an elastic tube arranged for expansion and retraction in radial directions so that the first end of the tube guide line is fitted onto the guide member of the magnetic sensor holder.

The magnetic measuring apparatus according to the sixth feature of the present invention allows the first end of the guide line made of the elastic tube to be elastically fitted onto the guide member of the magnetic sensor holder. Hence the joining of the guide lines to their respective magnetic sensor holders will be conducted at a higher efficiency.

For embodying a seventh feature of the present invention, a magnetic measuring apparatus of the prescribed type is provided in which each magnetic sensor is substantially joined to a first end of a pullup line which has a second end extending out or enabled to be withdrawn from the opening of the cryogenic vessel.

The magnetic measuring apparatus according to the seventh feature of the present invention allows the second end of the pullup line to be withdrawn from the opening so that when the pullup line is pulled, its joined magnetic sensor is withdrawn, hence contributing to the ease of replacement or repair of any of the magnetic sensors.

For embodying an eighth feature of the present invention, a magnetic measuring apparatus of the prescribed type is provided in which the magnetic sensor is integrated with a pipe body having a through hole through which the guide line is passed and joined to the first end of the pullup line.

The magnetic measuring apparatus according to the eighth feature of the present invention permits the magnetic sensor to be fed and moved along the guide line from the opening to the corresponding magnetic sensor holder with the through hole of its pipe body engaged with the guide line. Hence, the installation of the magnetic sensors on the bottom or side of the cryogenic vessel will be facilitated. Also, when the second end of the pullup line is pulled up, its joined magnetic sensor will readily be removed. As the result, replacement or repair of any of the magnetic sensors will be conducted at a higher efficiency.

For embodying a ninth feature of the present invention, a magnetic measuring apparatus of the prescribed type is provided in which the pipe body of the magnetic sensor is arranged so that it is split and removed from the magnetic sensor holder when the pullup line is pulled.

The magnetic measuring apparatus according to the ninth feature of the present invention allows the pipe body of the magnetic sensor to be split upon being pulled, hence facilitating the removal of the magnetic sensor from its magnetic sensor holder.

For embodying a tenth feature of the present invention, a magnetic measuring apparatus of the prescribed type is provided in which the bottom or side of the cryogenic vessel is formed to have two or more groups of the magnetic sensor holders at plural measuring areas so that plural test objects can simultaneously be placed in the measuring areas of the magnetic sensors of the groups of the magnetic sensor holders.

The magnetic measuring apparatus according to the tenth feature of the present invention allows the plural test objects to be simultaneously located in the measuring areas of the magnetic sensors of the groups, thus increasing the throughput. When a domed or arcuate region is formed on the side of the cryogenic vessel, it includes an undercut beneath an overhang at defining the opening of the cryogenic vessel. The magnetic sensors are mounted on the undercut portion without difficulty.

For embodying an eleventh feature of the present invention, a magnetic measuring apparatus having a plurality of magnetic sensors installed in a cryogenic vessel, signal lines of the magnetic sensors arranged extending out from an opening provided in the top of the cryogenic vessel, a coolant filled in the cryogenic vessel, and a lid closing the opening is provided further comprising two or more groups of magnetic sensor holders mounted on a bottom or side of the cryogenic vessel at plural measuring areas for allowing plural test objects to be simultaneously taken in the measuring areas of the magnetic sensors of the groups of the magnetic sensor holders.

The measuring apparatus according to the eleventh feature of the present invention allows the plural test objects to be simultaneously located in the measuring areas of the magnetic sensors of the groups, thus increasing the throughput.

BRIEF DESCRIPTION OF THE DRAWINGS

FIG. 31 is an explanatory view of the magnetic sensor unit fitted on the corresponding magnetic sensor holder;

FIG. 32 is an explanatory view of the magnetic sensor unit installed on the bottom of a cryogenic vessel.

DETAILED DESCRIPTION OF THE INVENTION

The embodiments of the present invention will be described in more details referring to the accompanying drawings. Although the following description involves measurement of magnetic fields spread in the ambient space about a human head, the same about a chest, an abdomen, a fetus, or any other like object can be measured with equal success.

Figure 1:
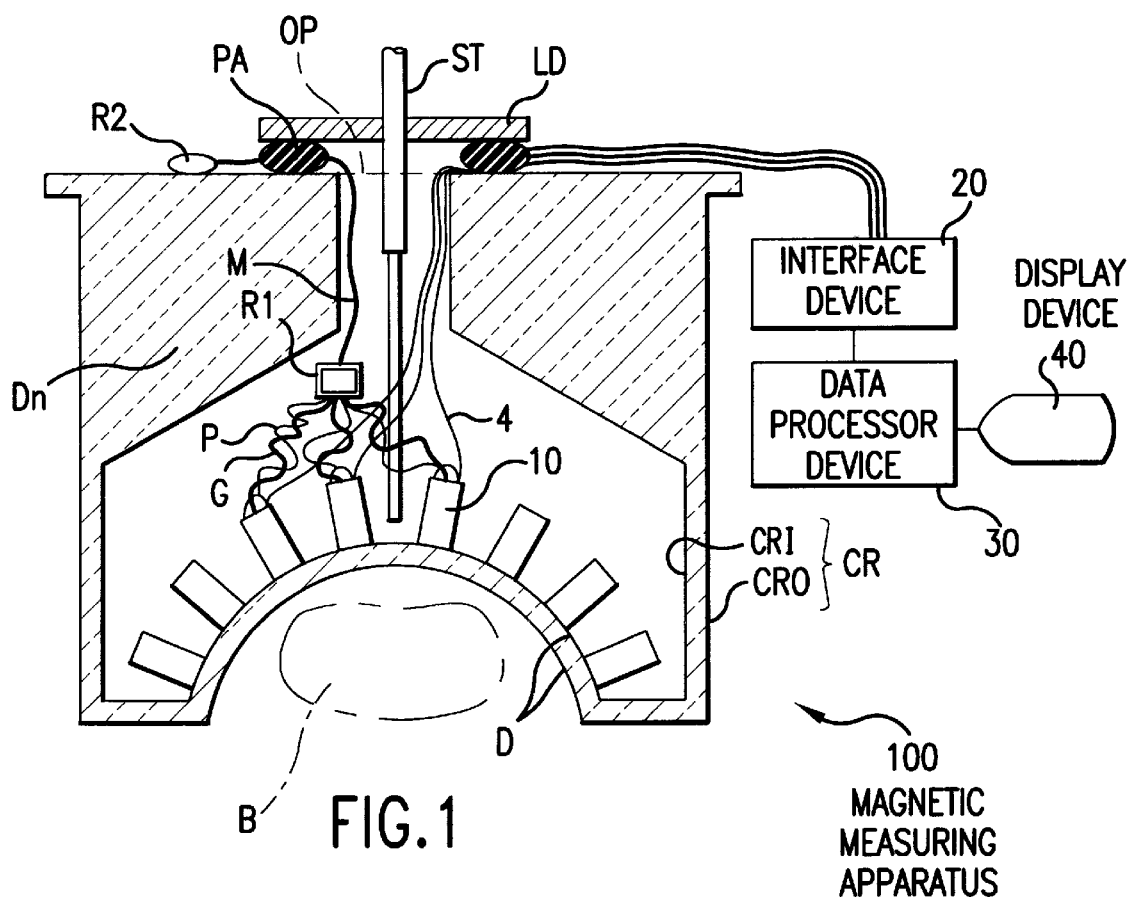
FIG. 1 is a schematic view of a magnetic measuring apparatus showing a first embodiment of the present invention.

FIG. 1 is a schematic view of a magnetic measuring apparatus showing a first embodiment of the present invention.

The magnetic measuring apparatus 100 comprises a cryogenic Dewar vessel CR composed of an inner vessel CRI and an outer vessel CRO having a domed bottom D for accepting a human head, a multiplicity of magnetic sensor units 10 mounted upright on an inner surface of the domed bottom D of the cryogenic vessel CR, an interface device 20 for receiving output signals from respective magnetic sensor units 10 through signal lines 4, a data processor device 30 for analyzing the output signals of the magnetic sensor units 10 to specify magnetic fields spread in the ambient space about the head and calculating activity data of a brain B from the magnetic fields, and a display device 40 for displaying the calculated activity data.

The space between the inner vessel CRI and the outer vessel CRO is filled with a thermal insulating material Dn and air is evacuated therefrom.

There are also provided guide lines G, pullup lines P, a ring R1 for bundling the guide lines G and the pullup lines P, a master cable M, and another ring R2 connected to one end of the master cable M.

The cryogenic vessel CR has a relatively small opening OP provided in a top thereof which overhangs the magnetic sensor units 10. Through the opening OP, the magnetic sensor units 10 are inserted and mounted upright on the inner surface of the domed bottom D of the inner vessel CRI. The opening OP also allows the signal lines 4 and the master cable M from the magnetic sensor units 10 to extend to the outside therethrough. The opening OP is closed with a combination of a lid LD and a packing PA. A coolant feed/exhaust double tube ST is provided through the lid LD for feeding a coolant to the cryogenic vessel CR. For replacement or repair, the magnetic sensor units 10 can be dismounted and mounted through the opening OP.

The packing PA may be made of a rubber material and the coolant may be a liquid helium (4.2K).

A procedure of manufacturing the magnetic measurement apparatus 100 will be explained referring to FIG. 2 to FIG. 12.

Figure 2:
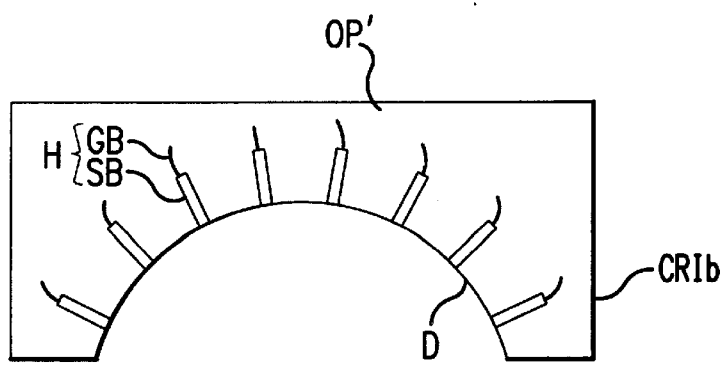
FIG. 2 is an explanatory view of an arrangement of magnetic sensor holders.

The procedure starts with forming a bottom part CRIb of the inner vessel CRI as shown in FIG. 2. A given number (for example, 16 to 150) of magnetic sensor holders H are mounted on an arcuate region of the domed bottom D. The magnetic sensor holder H comprises a support base SB mounted upright on the bottom D and a flexible guide GB extending upwardly from the support base SB.

Figure 3:
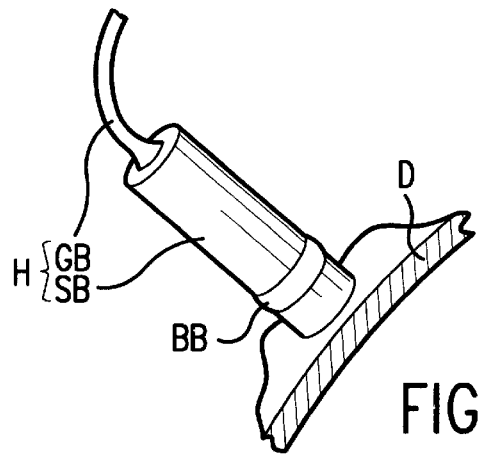
FIG. 3 is a perspective view of the magnetic sensor holder.

As shown in FIG. 3, the support base SB is made of preferably a nylon material having a cylindrical shape of 95 mm in length and 8 mm in diameter. A bulged region BB, of which a diameter is preferably 10.5 mm, is formed near a base end of the support base SB.

The guide GB is made of preferably a nylon material having a whisker-like shape of 50 mm in length and 3 mm in diameter and arranged to curve upwardly.

Figure 4:
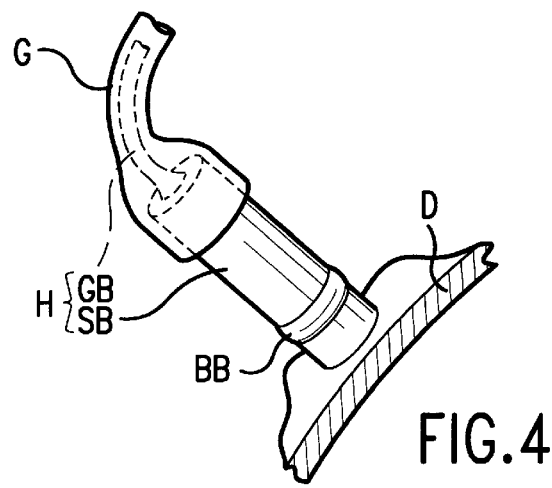
FIG. 4 is an explanatory view of the magnetic sensor holder joined with a guide line.

Each of guide lines G is then joined at one end to the corresponding magnetic sensor holder H, as shown in FIG. 4. The guide line G is preferably a flexible tube fabricated by knitting nylon yarns so that its diameter can vary from 1 mm to 15 mm. A first tube end of the guide line G is fitted over the guide GB and an upper portion of the support base SB.

Figure 5:
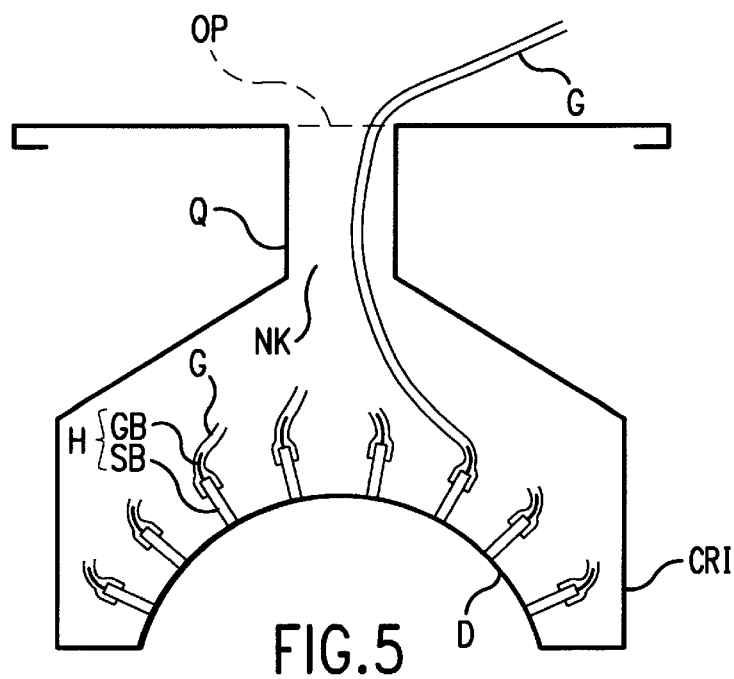
FIG. 5 is an explanatory view of installation of the guide line.

This is followed by forming a side Q of the inner vessel CRI, as shown in FIG. 5. As the result, the entirety of the inner vessel CRI is completed with the relatively small opening OP in the top thereof. Simultaneously, the second end of the guide line G, of which the first end is joined to the magnetic sensor holder H, is withdrawn through the opening OP.

The diameter of the small opening OP is preferably 3 cm to 5 cm. A neck region NK of the inner vessel CRI has a same diameter as the opening OP and a depth of about 30 cm to 50 cm.

Figure 6:
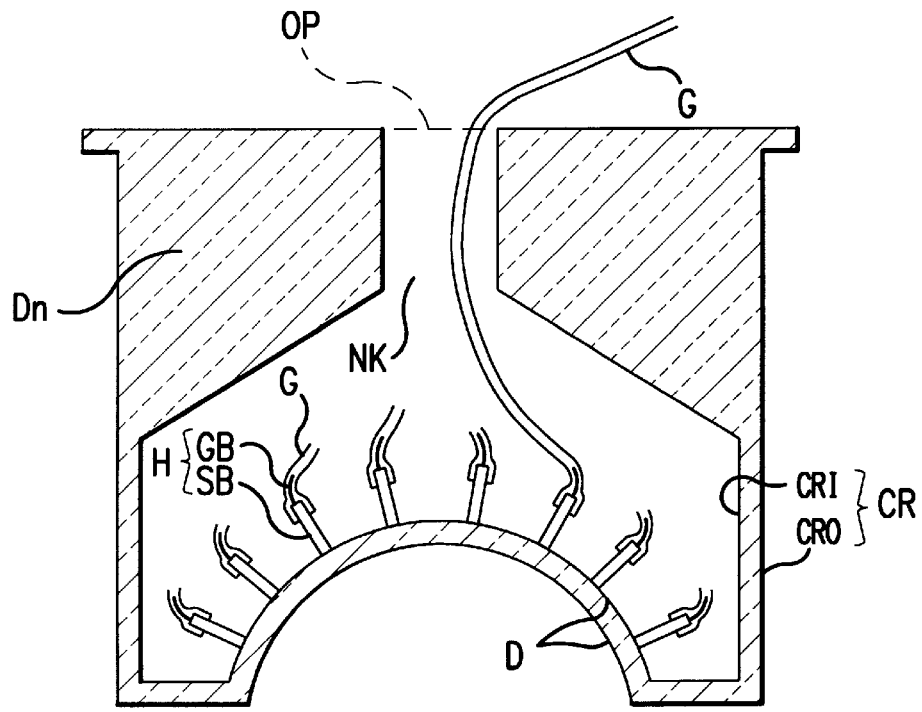
FIG. 6 is an explanatory view of providing a small opening at the top.

Then, the thermal insulating material Dn is installed around the inner vessel CRI and the outer vessel CRO is mounted to complete the cryogenic vessel CR with the small opening OP, as shown in FIG. 6.

Figure 7:
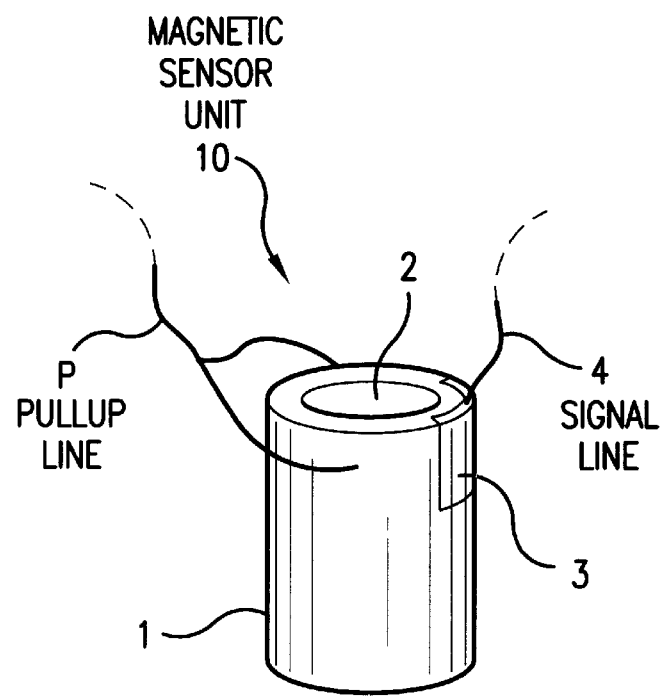
FIG. 7 is a perspective view of a magnetic sensor unit.

This is followed by preparing the magnetic sensor units 10, one of which being shown in FIG. 7.

The magnetic sensor unit 10 is fabricated by mounting a magnetic sensor (not shown), such as a superconductive quantum interference device, and an electronic circuit 3 to a pipe member 1 having a through hole 2 therein and joining the signal line 4 to the electronic circuit 3 and the pullup line P to the pipe member 1.

The pipe member 1 is preferably an epoxy resin tubing having a length of 100 mm, an outer diameter of 20 mm, and an inner diameter of 10 mm.

The pullup line P is preferably a nylon string.

Figure 8:
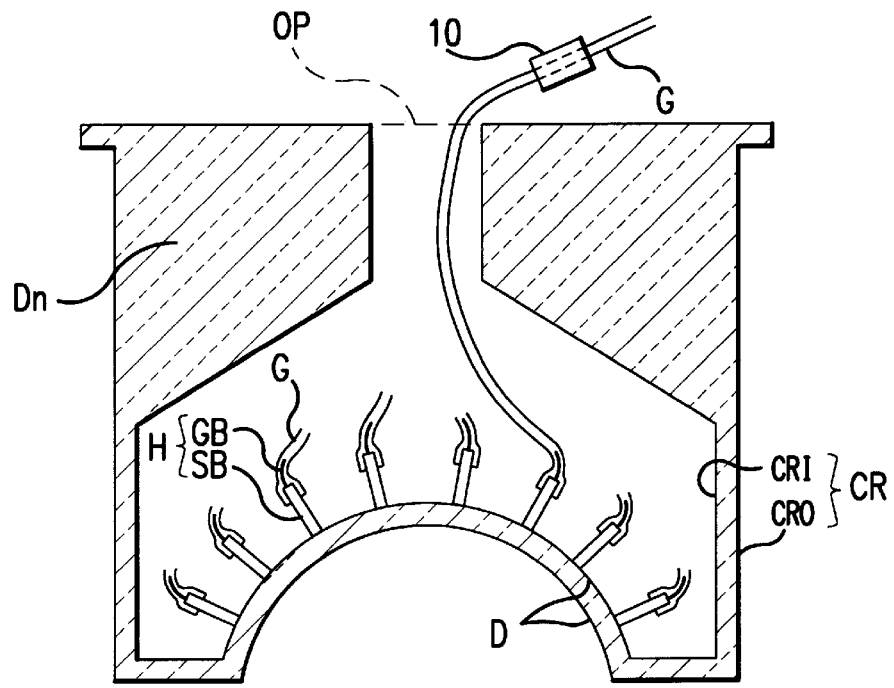
FIG. 8 is an explanatory view of the magnetic sensor unit being installed along the guide line.
Figure 9:
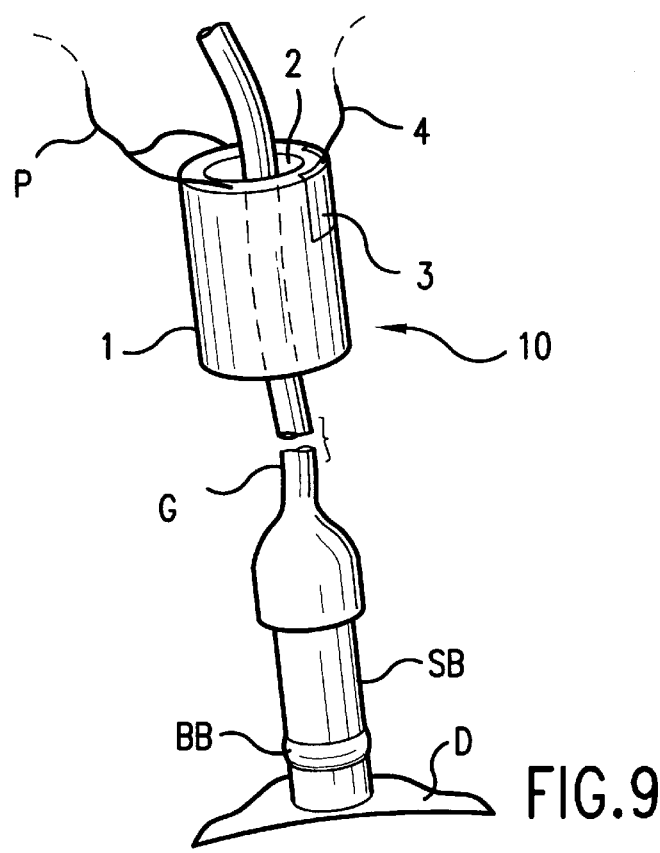
FIG. 9 is an enlarged explanatory view of the magnetic sensor unit being installed along the guide line.

As shown in FIGS. 8 and 9, each of the guide lines G is passed through the through hole 2 of the corresponding magnetic sensor unit 10.

Figure 10:
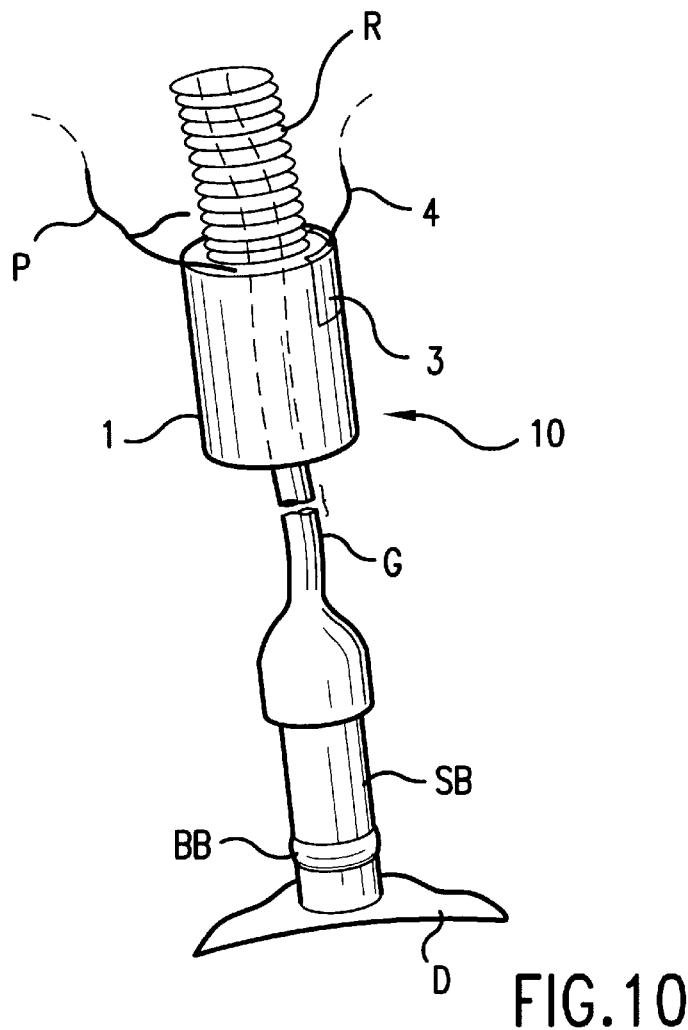
FIG. 10 is an explanatory view of the magnetic sensor unit being urged downwardly by a pressing tool.
Figure 11:
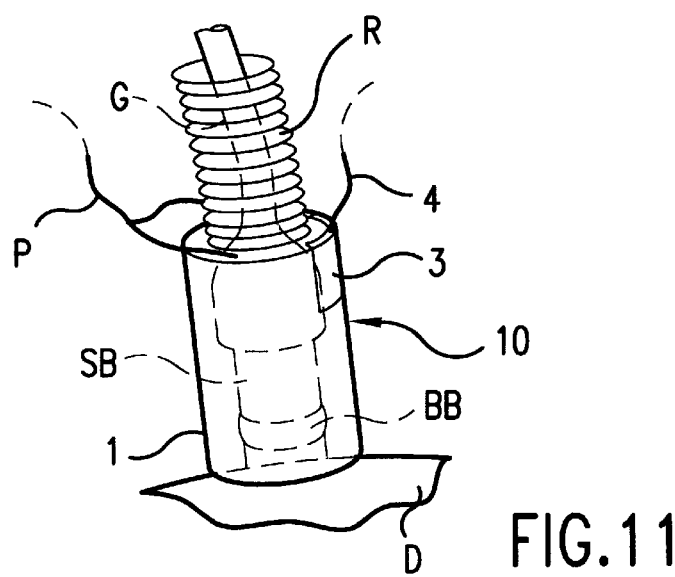
FIG. 11 is an explanatory view of the magnetic sensor unit fitted on a sensor support.
Figure 12:
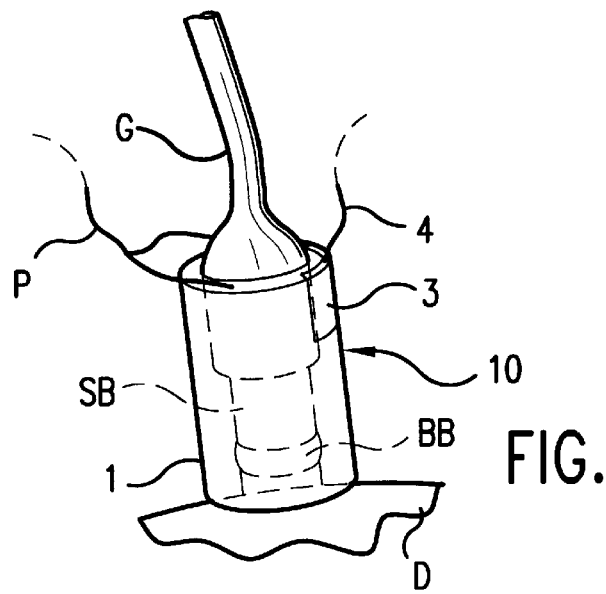
FIG. 12 is an explanatory view of the magnetic sensor unit installed on the bottom of a cryogenic vessel.

The magnetic sensor unit 10 is then lowered and fitted on to the support base SB of the magnetic sensor holder H by means of a pressing jig R such as a coil spring as shown in FIGS. 10 and 11 or plastic tube. As the through hole 2 of the magnetic sensor unit 10 is 10 mm in diameter and the bulged portion BB of the support base SB is 10.5 mm in outer diameter, the magnetic sensor unit 10 is securely anchored to the support base SB. The pressing jig R is then removed out as shown in FIG. 12.

This is followed by placing the guide lines G and the pullup lines P in the ring R1 and connecting the ring R1 to one end of the master cable M as shown in FIG. 1. The ring R1 is then dropped from the small opening OP into the cryogenic vessel CR and the other end of the master cable M is joined to the ring R2 which is held outside the cryogenic vessel CR.

Finally, the opening OP is closed with the lid LD and the packing PA and the coolant is supplied via the coolant feed/exhaust double tube ST to fill the cryogenic vessel CR.

For replacement or repairing any of the magnetic sensor units 10, the ring R2 is pulled upwardly to withdraw the ring R1 joined to the master cable M. When the guide line G and the pullup line P of the target magnetic sensor unit 10 are selected, the magnetic sensor unit 10 is removed out through the opening OP by pulling the pullup line P.

Accordingly, the magnetic measuring apparatus 100 has the relatively small opening OP which allows the entering of a minimum of heat and thus minimizes the evaporation loss of the coolant in the cryogenic vessel CR contributing to the lower running cost.

Figure 13:
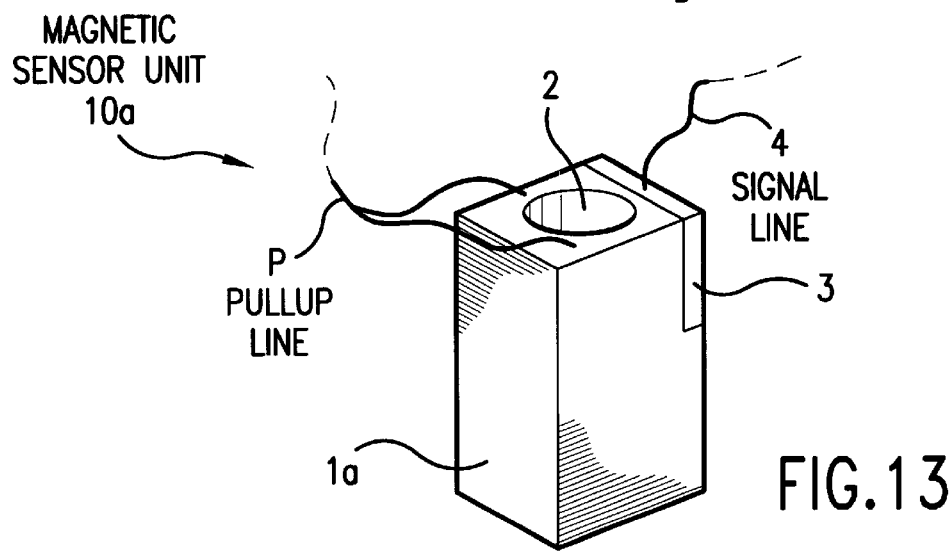
FIG. 13 is a perspective view of a magnetic sensor unit showing a second embodiment of the present invention.

The present invention provides a second embodiment where the magnetic sensor unit 10 is replaced by another magnetic sensor unit 10a illustrated in FIG. 13.

The magnetic sensor unit 10a includes a pipe member 1a of a square tube configuration.

Figure 14:
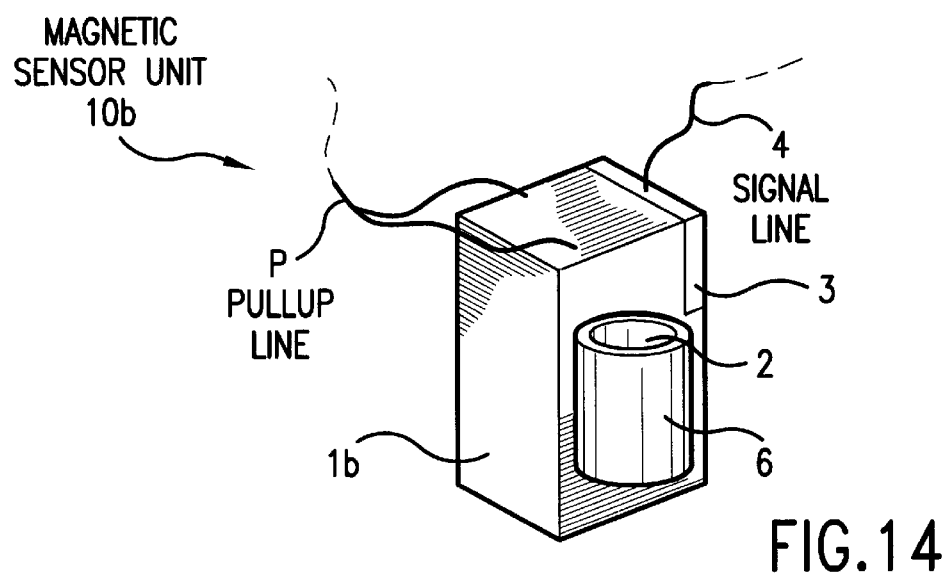
FIG. 14 is a perspective view of a magnetic sensor unit showing a third embodiment of the present invention.

The present invention provides a third embodiment where the magnetic sensor unit 10 is replaced by a further magnetic sensor unit 10b shown in FIG. 14.

The magnetic sensor unit 10b includes a block member 1b provided with a pipe 6 through which the guide line G is passed.

Figure 15:
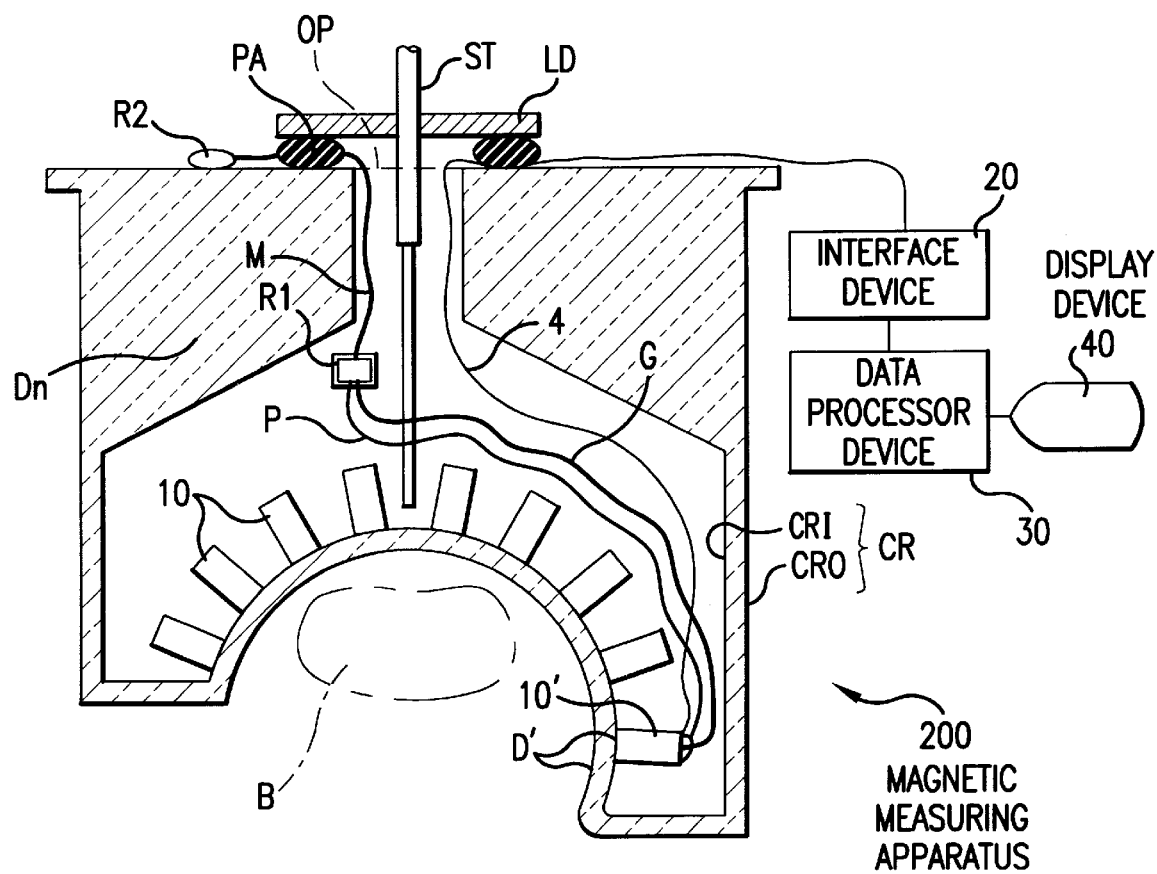
FIG. 15 is a schematic view of a magnetic measuring apparatus showing a fourth embodiment of the present invention.

FIG. 15 is a schematic view of a magnetic measuring apparatus showing a fourth embodiment of the present invention.

The magnetic measuring apparatus 200 has a bottom D' of an inner vessel CRI and a bottom of an outer vessel CRO of a cryogenic vessel CR formed for accepting a human head up to its rear lower end. The other components and their arrangement are the same as those of the magnetic measuring apparatus 100 of the first embodiment.

A rear lower end region of the bottom D' is shaped into an undercut where a magnetic sensor unit 10' is allocated to a region tilted below the horizontal line. However, due to respective guide line G, the magnetic sensor unit 10' can readily be installed with ease. For replacement or repair, the magnetic sensor unit 10' is easily removed.

Figure 16:
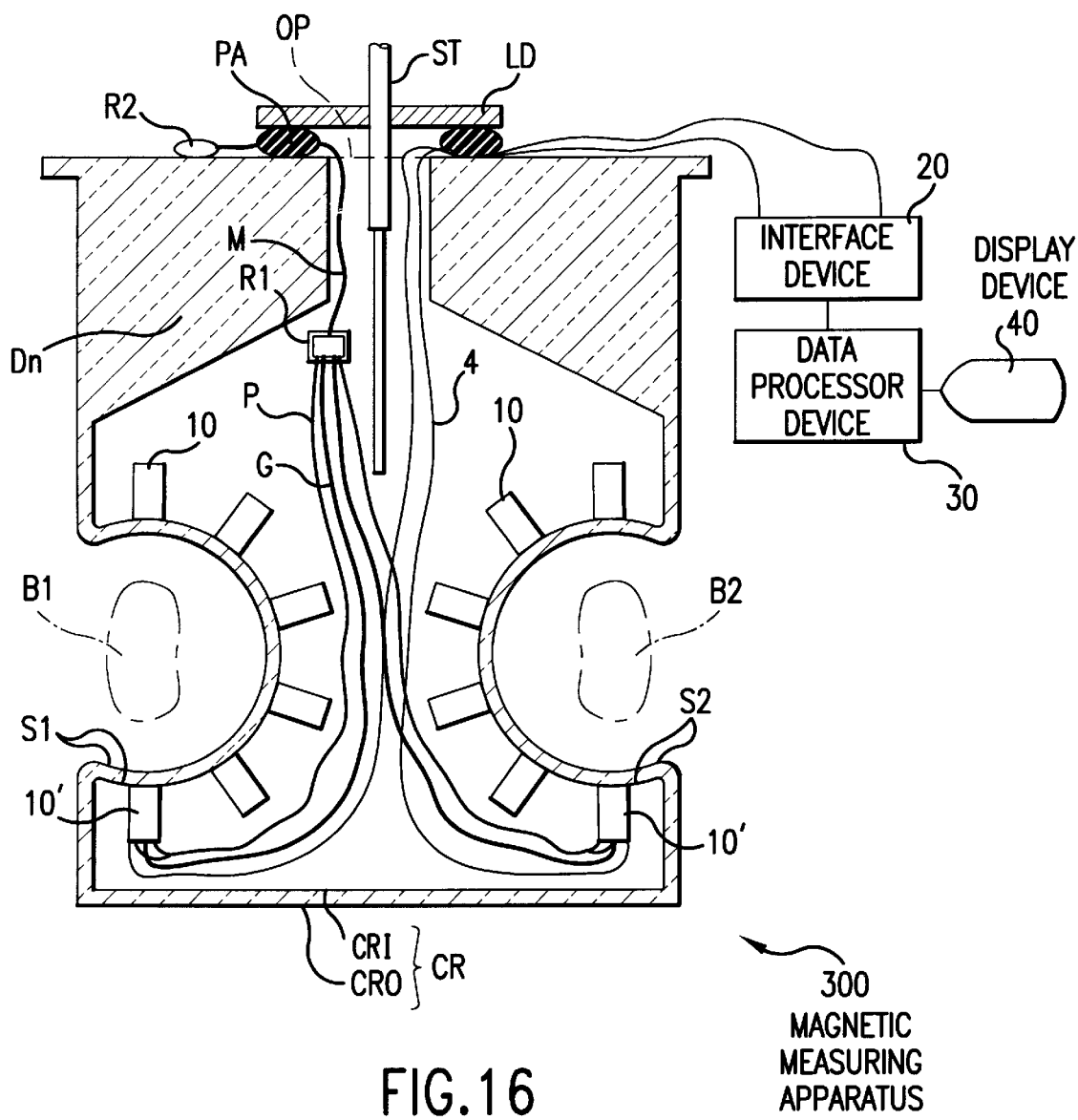
FIG. 16 is a schematic view of a magnetic measuring apparatus showing a fifth embodiment of the present invention.

FIG. 16 is a schematic view of a magnetic measuring apparatus showing a fifth embodiment of the present invention.

The magnetic measuring apparatus 300 has a cryogenic vessel CR composed of an inner vessel CRI and an outer vessel CRO having two domed regions S1 and S2 at opposite sides for accepting human heads respectively. Groups of the magnetic sensor units 10 and 10' are mounted upright on the inner surfaces of the domed regions S1 and S2. The other components and their arrangement are identical to those of the magnetic measuring apparatus 100 of the first embodiment.

As shown, the magnetic sensor units 10' are mounted nearly upside down. However, due to their respective guide lines G, the magnetic sensor units 10' can readily be installed without difficulty. For replacement or repair, the magnetic sensor units 10' are removed with ease.

A data processor device 30 is provided for parallel processing the output signals from the magnetic sensor units 10 of one group on the domed region S1 and of the other group on the domed region S2. This allows two test objects to be simultaneously measured for the magnetic fields.

If desired, three or more of the domed regions may be provided.

Figure 17A:
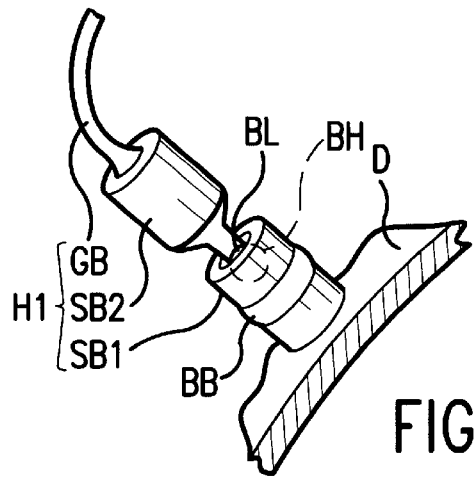
FIG. 17(a) and (b) are perspective views of a magnetic sensor holder showing a sixth embodiment of the present invention.

The present invention provides a sixth embodiment where the magnetic sensor holder H is replaces by another magnetic sensor holder H1 shown in FIG. 17(a) and (b).

As apparent from FIG. 17(a), the magnetic sensor holder H1 comprises a first support base SB1 having a ball holding pit BH therein and mounted upright to the domed bottom D, a second support base SB2 having a ball BL thereof accommodated in the ball holding pit BH, and a flexible guide GB extending outwardly from the second support base SB2.

Figure 17B:
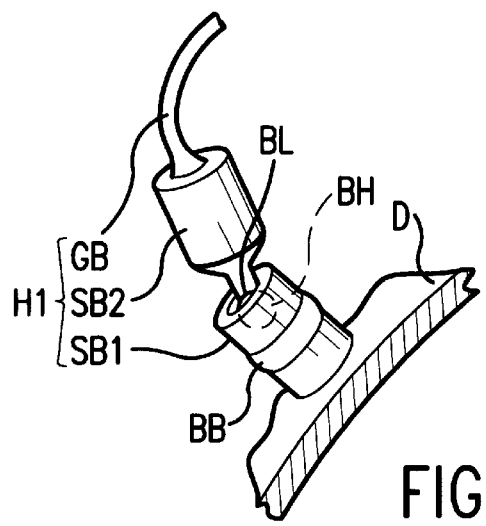

The second support base SB2 is hence pivotable on the ball BL as shown in FIG. 17(b).

Figure 18:
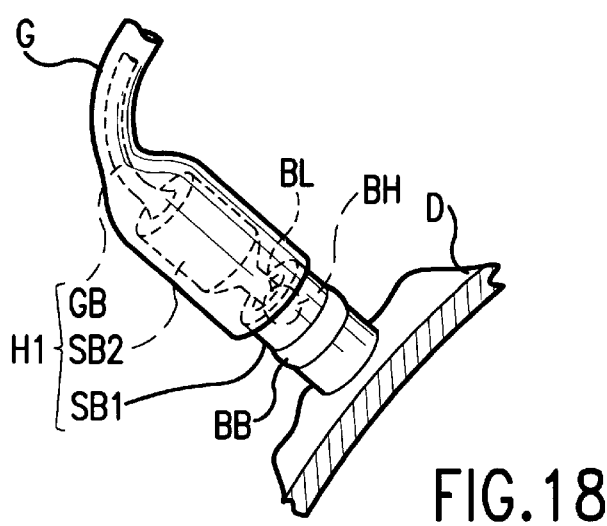
FIG. 18 is an explanatory view of the magnetic sensor holder of FIG. 17 joined with a guide line.

As shown in FIG. 18, the magnetic sensor holder H1 is joined to a first end of the guide line G. The first end of the guide line G is fitted over the flexible guide GB onto the first support base SB1.

As its second support base SB2 of the magnetic sensor holder H1 is pivotable, the magnetic sensor unit H1 allows the corresponding magnetic sensor unit 10 or 10' to be smoothly fitted thereonto without jerking movements on the way.

Figure 19A:
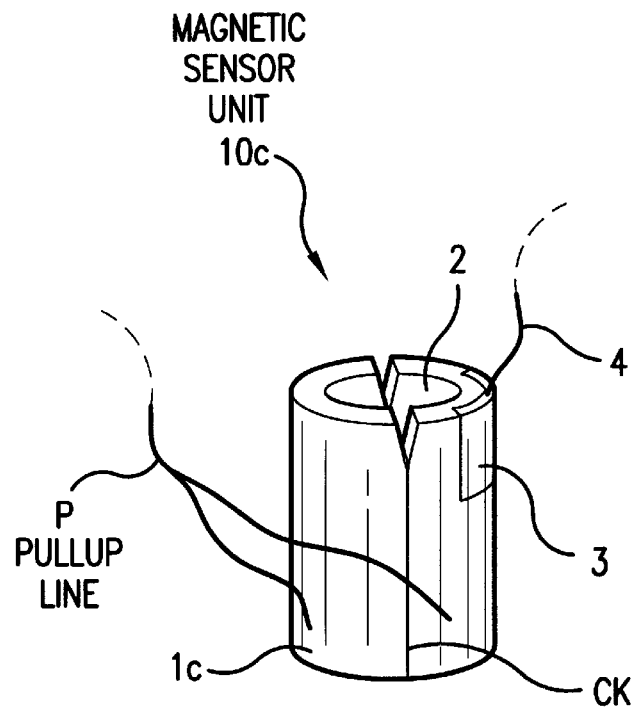
FIG. 19(a) and (b) are perspective views of a magnetic sensor unit showing a seventh embodiment of the present invention.

The present invention provides a seventh embodiment where the magnetic sensor unit 10 is replaced by a still further magnetic sensor unit 10c illustrated in FIG. 19(a) and (b).

As best shown in FIG. 19(a), the magnetic sensor unit 10c includes a pipe member 1c having slits CK therein. Two branches of the pullup line P are joined to both segments of the pipe member 1c defined by the slits CK.

Figure 19B:
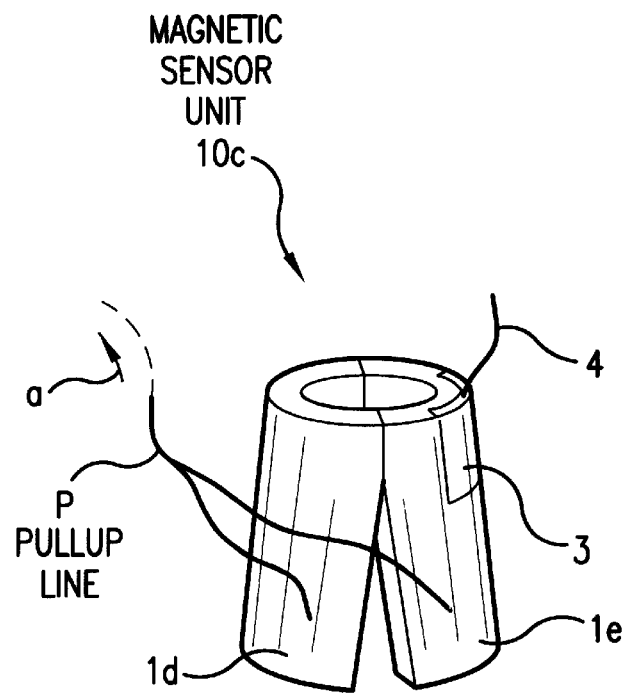

In action, when the pullup line P is pulled in the direction denoted by the arrow "a" of FIG. 19(b), the pipe member 1c is separated into the two segments 1d and 1e along the slits CK so that the magnetic sensor unit 10c is easily removed from the corresponding magnetic sensor holder H.

Figure 20:
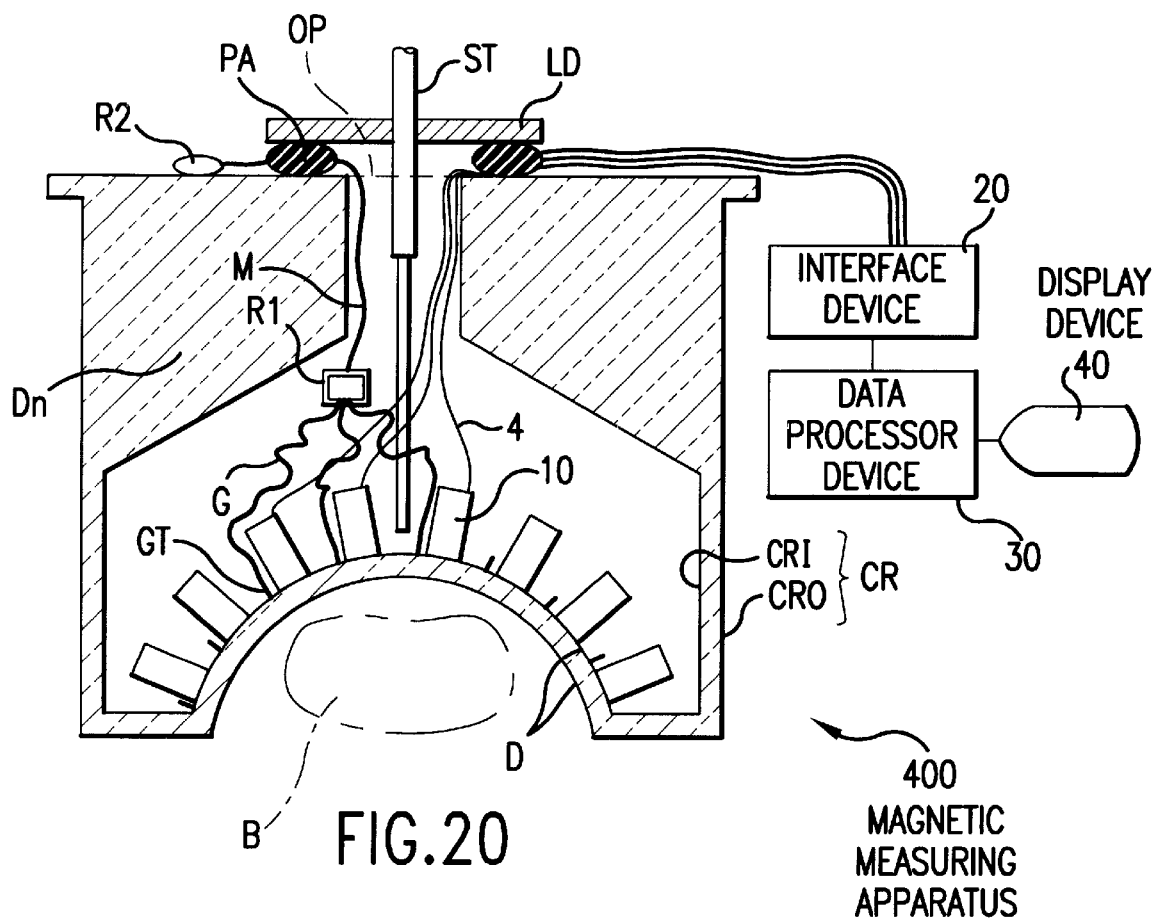
FIG. 20 is a schematic view of a magnetic measuring apparatus showing an eighth embodiment of the present invention.

FIG. 20 is a schematic view of a magnetic measuring apparatus showing an eighth embodiment of the present invention.

The magnetic measuring apparatus 400 includes guide line mounts GT mounted adjacent to their respective sensor units 10 upright on the bottom D of the inner vessel CRI of the cryogenic vessel CR. The guide line mount GT is joined to a first end of the guide line G. No pullup line is joined to the magnetic sensor unit 10. The other components and their arrangement are identical to those of the magnetic measuring apparatus 100 of the first embodiment.

A procedure of fabricating the magnetic measuring apparatus 400 will now be explained referring to FIG. 21 to FIG. 32.

Figure 21:
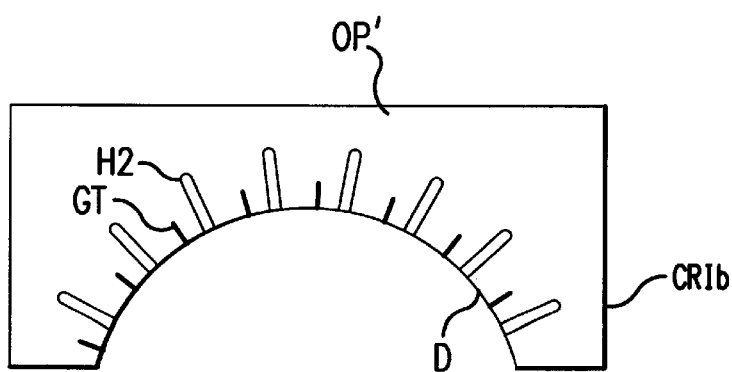
FIG. 21 is an explanatory view of an arrangement of magnetic sensor holders and guide line mounts.

The procedure starts with forming a bottom part CRIb of the inner vessel CRI and mounting a plurality of magnetic sensor holders H2 on a domed region of the bottom D, as shown in FIG. 21. The guide line mounts GT are then installed adjacent to their respective magnetic sensor holders H2.

Figure 22:
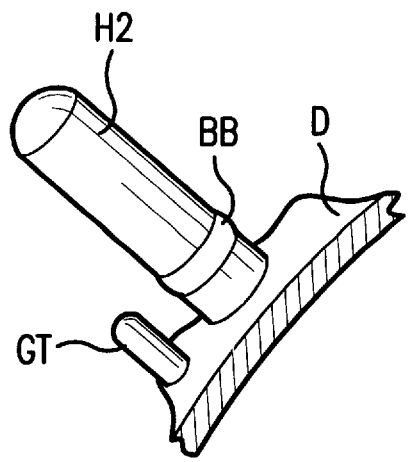
FIG. 22 is a perspective view of the magnetic sensor holder adjacent to the guide line mount.

The magnetic sensor holder H2 may be a nylon cylinder of 95 mm in length and 8 mm in diameter, configured as shown in FIG. 22. The magnetic sensor holder H2 has a bulged region BB near a base end thereof having diameter that is preferably 10.5 mm.

The guide line mount GT is preferably a nylon cylinder of 25 mm in length and 4 mm in diameter.

Figure 23:
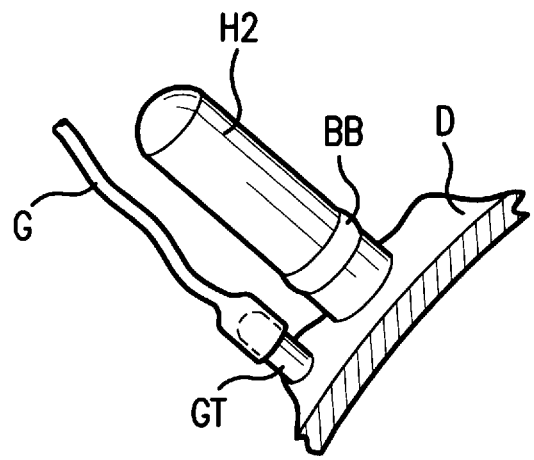
FIG. 23 is an explanatory view of the guide line mount joined with a guide line.

As shown in FIG. 23, the first end of the guide line G is joined to the guide line mount GT. The guide line G is preferably a tube made by knitting nylon yarns so that its diameter can vary from 1 mm to 15 mm. The first end of the tube guide line G is fitted onto the corresponding guide line mount GT.

Figure 24:
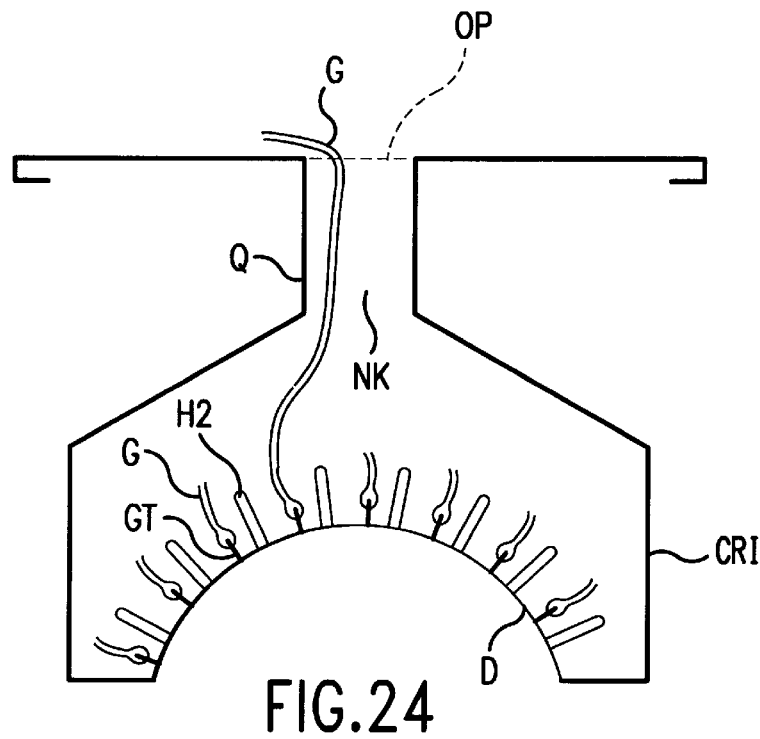
FIG. 24 is an explanatory view of installation of the guide line.

This is followed by adding a side Q of the inner vessel CRI thus to form the entirety of the inner vessel CRI having a relatively small opening OP on the top, as shown in FIG. 24. At that time, the second ends of the guide lines G, connected at their first ends to the corresponding magnetic sensor holders H2, are exposed out through the opening OP.

The relatively small opening OP is preferably 3 cm to 5 cm in diameter. A neck region NK of the inner vessel CRI is provided of which an inner diameter is identical to that of the opening OP and extends downwardly about 30 cm to 50 cm.

Figure 25:
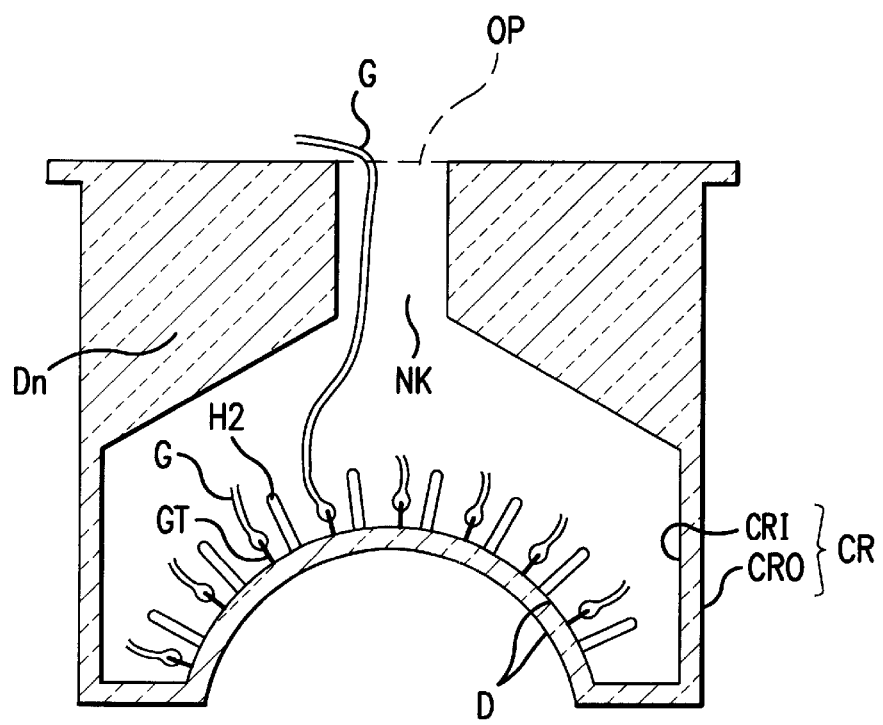
FIG. 25 is an explanatory view of providing a relatively small opening at the top.

Then, a thermal insulating material Dn is positioned as shown and an outer vessel CRO is added thus forming the cryogenic vessel CR with the opening OP, as shown in FIG. 25.

Figure 26:
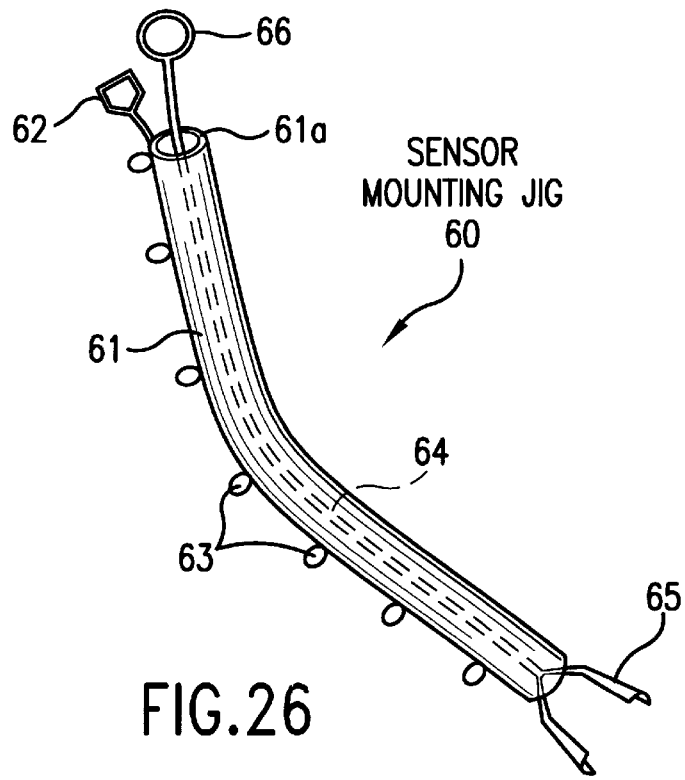
FIG. 26 is a perspective view of a sensor mounting jig.

This is followed by preparing a sensor mounting jig 60 shown in FIG. 26.

The sensor mounting jig 60 comprises a tube 61 having a through hole 61a therein, a tube holding handle 62 joined to a first end of the tube 61, a plurality of rings 63 mounted on an outer periphery of the tube 61, a wire 64 joined at a first end to a handle 66 and extending through the through hole 61a of the tube 61, and a gripper 65 joined to a second end of the wire 64.

When the tube holding handle 62 is pulled relative to the handle 66 being held stationary, the gripper 65 is exposed out from the through hole 61a and opens.

Figure 27:
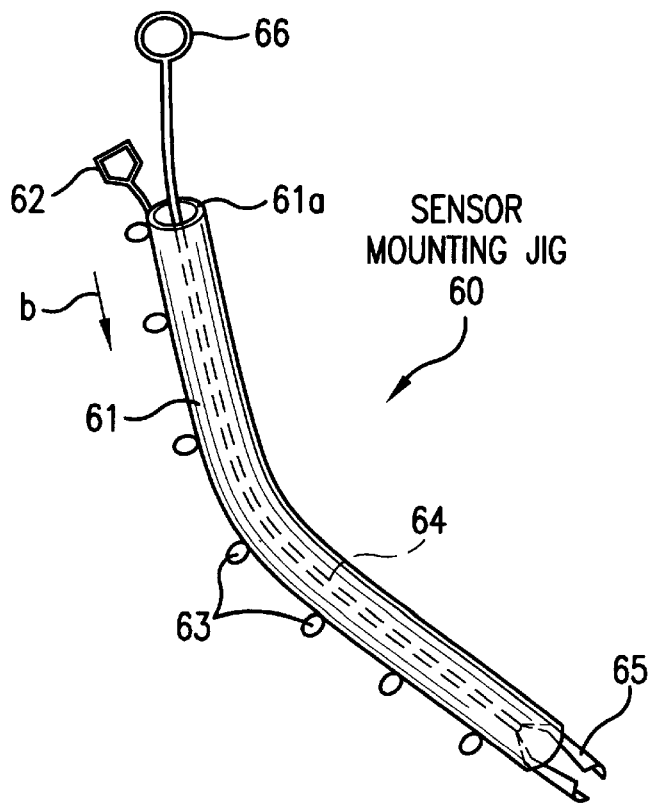
FIG. 27 is an explanatory view of the sensor mounting jig of FIG. 26 with its gripper being closed.

When the tube holding handle 62 is pushed in the direction denoted by the arrow b in FIG. 27 relative to the handle 66 being held stationary, the gripper 65 is retracted into the through hole 61a and closes.

This closing and opening action allows the gripper 65 to hold and release the magnetic sensor unit 10.

Figure 28:
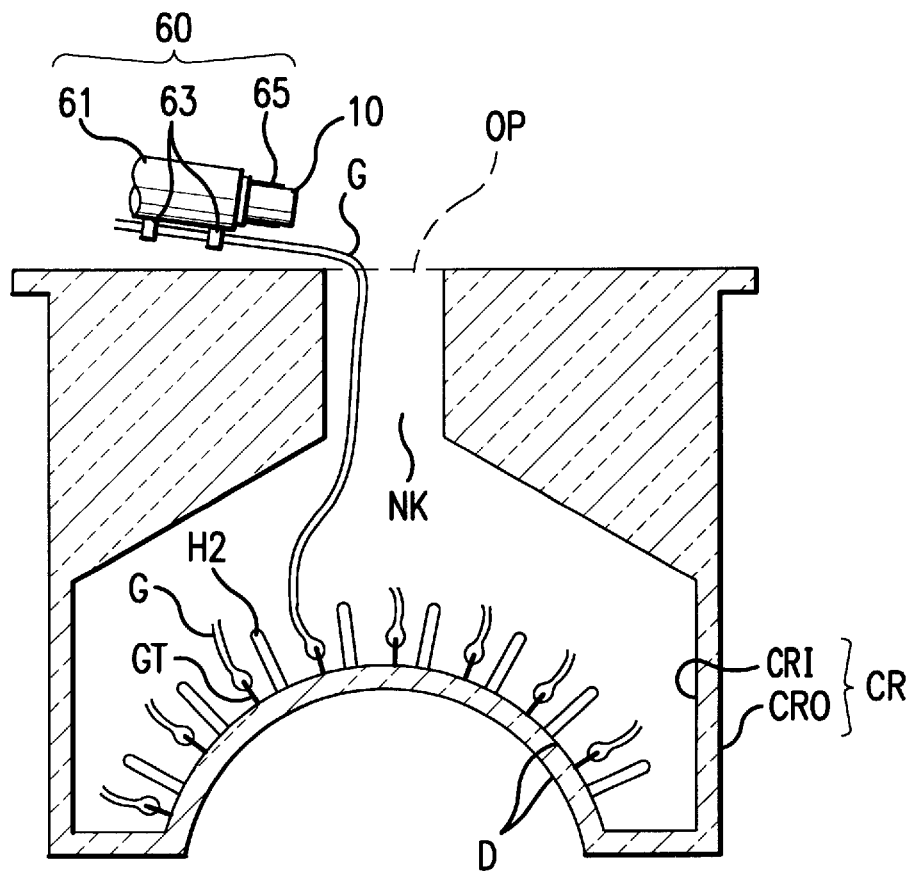
FIG. 28 is an explanatory view of the guide line passing through rings of the sensor mounting jig which holds a magnetic sensor unit.

The guide line G is then passed through the rings 63 of the sensor mounting jig 60 as shown in FIG. 28 while the gripper 65 of the sensor mounting jig 60 holds the magnetic sensor unit 10.

Figure 29:
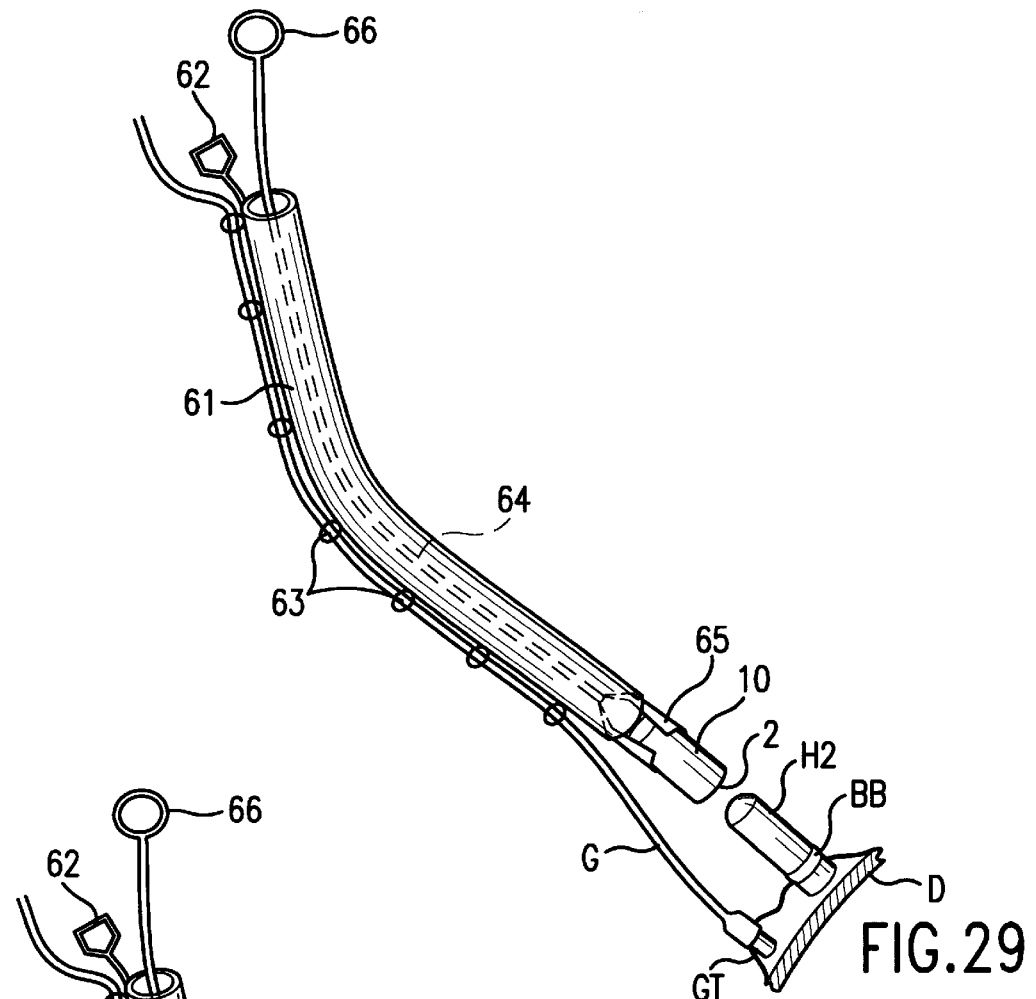
FIG. 29 is an enlarged explanatory view of the sensor mounting jig which holds the magnetic sensor unit while the guide line passes through its rings.

As the tube holding handle 62 and the handle 66 are moved forward, the magnetic sensor unit 10 held by the gripper 65 travels along the guide line G towards the magnetic sensor holder H2 as shown in FIG. 29.

Figure 30:
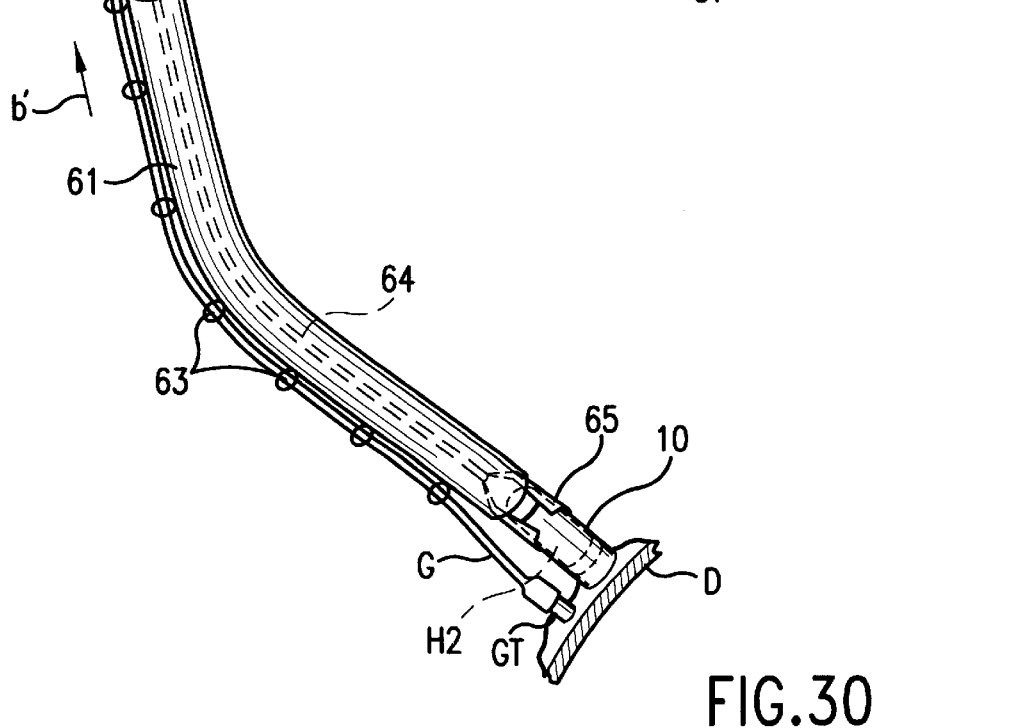
FIG. 30 is an explanatory view of the magnetic sensor unit being installed with the sensor mounting jig.
Figure 33:
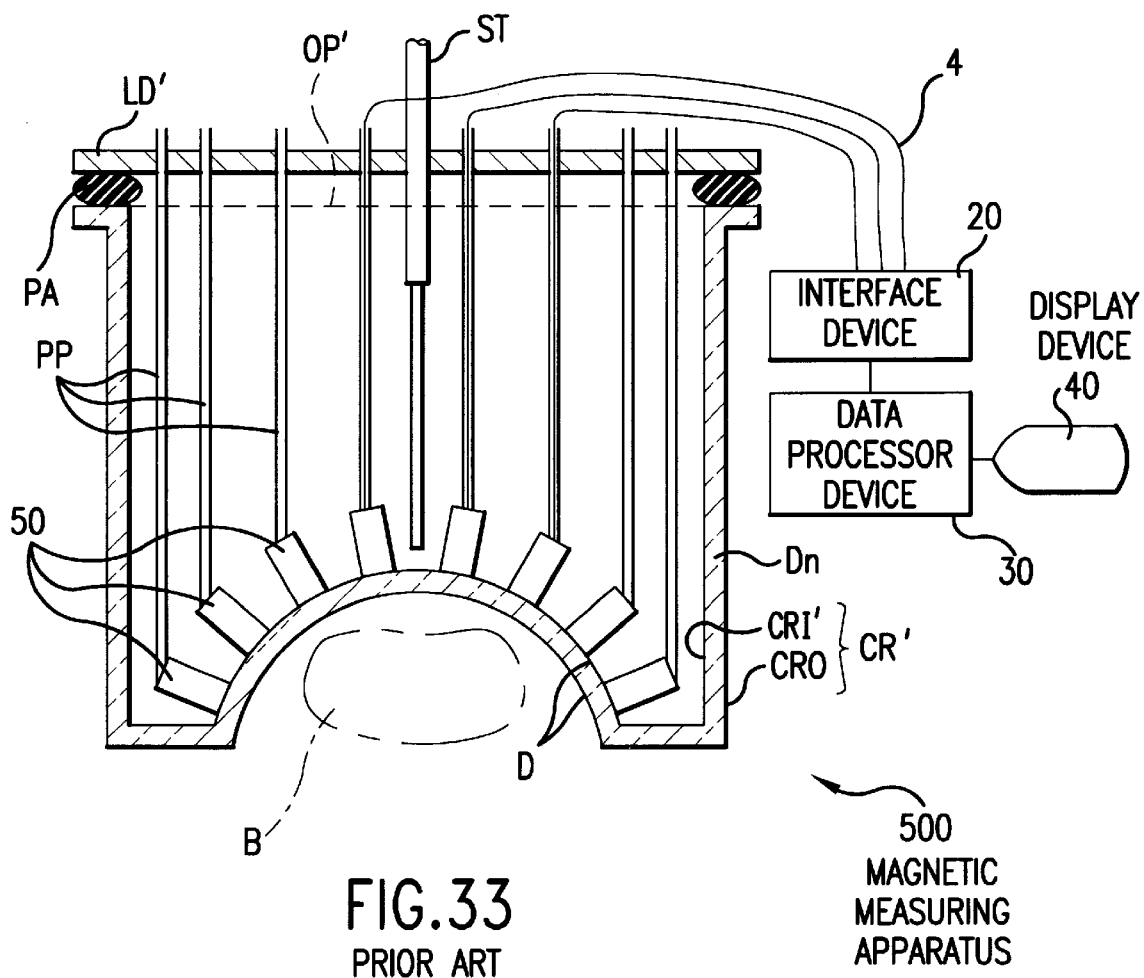
FIG. 33 is a schematic view of a prior art magnetic measuring apparatus.

When the tube holding handle 62 and the handle 66 have been pressed down, the magnetic sensor unit 10 held by the gripper 65 is fitted onto the magnetic sensor holder H2 as shown in FIG. 30. Because the diameter of a through hole 2 of the magnetic sensor unit 10 is 10 mm and the bulged region BB of the magnetic sensor holder H2 is 10.5 mm, the magnetic sensor unit 10 is tightly secured to the magnetic sensor holder H2.

This action may preferably be carried out using a fiber scope.

Then, the magnetic sensor unit 10 is released from the gripper 65 as shown in FIG. 31.

The sensor mounting jig 60 is removed from the guide line G by pulling the tube holding handle 62 and the handle 66, as shown in FIG. 32.

Similarly, the other magnetic sensor units 10 are mounted to their corresponding magnetic sensor holders H2.

This is followed by bundling all the guide lines G with a ring R1, joining the ring R1 to the first end of a master cable M, dropping the ring R1 through the opening OP into the interior of the cryogenic vessel CR, joining the second end of the master cable M to a ring R2, and holding the ring R2 outside the cryogenic vessel CR.

Finally, the opening OP is closed with a lid LD and a packing PA and the cryogenic vessel CR is filled with a coolant supplied via a coolant feed/exhaust double tube ST.

For replacement or repair of any of the magnetic sensor units 10, the ring R2 is pulled to withdraw the ring R1 joined to the first end of the master cable M allowing the corresponding guide line G joined to the required magnetic sensor unit 10 to be selected. The guide line G is passed through the rings 63 of the sensor mounting jig 60. As the sensor mounting jig 60 has been moved in, its gripper 65 holds and withdraws the magnetic sensor unit 10.

Accordingly the magnetic measuring apparatus 400 has the relatively small opening OP hence allowing the entry of minimum amounts of heat and reducing the evaporation loss of the coolant in the cryogenic vessel CR and thus contributing to the lower running cost.

The magnetic measuring apparatus of the present invention allows the magnetic sensors to be readily installed in the cryogenic vessel through its relatively small opening and any of them to be dismounted for replacement or repair without difficulty. As the relatively small opening permits the passing of a minimum amount of heat and decreases the evaporation loss of a coolant, the running cost will considerably be reduced. Since the magnetic sensors are mounted to any configuration, an undercut portion of the cryogenic vessel is applicable for matching the shape of a test object. This also permits a specific construction for accepting two or more test objects and will thus contribute to the higher throughput of the magnetic measuring apparatus.

What is claimed is:

1. A magnetic measuring apparatus comprising:

a cryogenic vessel having a top surface with an access opening, an inner bottom surface and an inner side surface;

magnetic sensors installed in the cryogenic vessel;

signal lines extending from the magnetic sensors through the access opening;

a coolant filling the cryogenic vessel;

a lid closing the access opening;

magnetic sensor holders mounted on one of the inner bottom surface and the inner side surface of the cryogenic vessel upon which respective ones of the magnetic sensors are mounted;

guide lines, each of the guide lines having a first end connected to one of a respective one of the magnetic sensor holders and a portion of the one of the inner bottom surface and the inner side surface proximate a respective one of the magnetic sensor holders;

connecting means for slidably connecting said magnetic sensors to respective ones of said guide lines; and each of the guide lines having a second end extending out through the access opening of the cryogenic vessel so that a respective one of the magnetic sensors is movable along an associated one of said guide lines from a first position at the access opening to a second position mounted on the respective one of the magnetic sensor holders.

2. The magnetic measuring apparatus according to claim 1, wherein the magnetic sensors are each integrated with a pipe body and the connecting means includes the pipe body having a through hole through which the associated one of the guide lines is passed.

3. The magnetic measuring apparatus according to claim 2, wherein each of the magnetic sensor holders includes a support base secured to the one of the inner bottom surface and the inner side surface of the cryogenic vessel for holding the respective one of the magnetic sensors the support base being fitted into the through hole of the pipe body.

4. The magnetic measuring apparatus according to claim 3, wherein the support base includes a first support base secured to the one of the inner bottom surface and the inner side surface of the cryogenic vessel and a second support base pivotably mounted to the first support base.

5. The magnetic measuring apparatus according to claim 3 or claim 4, wherein the guide lines are elastic tubes expandable and contractible in radial directions thereof so that the first ends of the guide lines are fitable over portions of the magnetic sensor holders.

6. The magnetic measuring apparatus according to claim 1, wherein the one of the inner bottom surface and the inner side surface of the cryogenic vessel is the inner side surface and has two arrays of the magnetic sensor holders with respective ones of the magnetic sensors mounted thereon, the two arrays being disposed apart from one another for simultaneously performing measurements of two test objects situated within measurements ranges of the magnetic sensors mounted on respective ones of the two arrays of magnetic sensor holders.

7. A magnetic measuring apparatus comprising:

a cryogenic vessel having a top surface with an access opening, an inner bottom surface and an inner side surface;

magnetic sensors installed in the cryogenic vessel;

signal lines extending from the magnetic sensors through the access opening;

a coolant filling the cryogenic vessel;

a lid closing the access opening;

magnetic sensor holders mounted on one of the inner bottom surface and the inner side surface of the cryogenic vessel upon which respective ones of the magnetic sensors are mounted;

guide lines, each of the guide lines having a first end connected to one of a respective one of the magnetic sensor holders and a portion of the one of the inner bottom surface and the inner side surface proximate a respective one of the magnetic sensor holders;

connecting means for slidably connecting said magnetic sensors to respective ones of said guide lines; and each of the guide lines having a second end withdrawable through the access opening of the cryogenic vessel so that a respective one of the magnetic sensors is movable along an associated one of said guide lines between a first position at the access opening to a second position mounted on the respective one of the magnetic sensor holders.

8. The magnetic measuring apparatus according to claim 7, wherein the magnetic sensors are each integrated with a pipe body and the connecting means includes the pipe body having a through hole through which the associated one of the guide lines is passed.

9. The magnetic measuring apparatus according to claim 8, wherein each of the magnetic sensor holders includes a support base secured to the one of the inner bottom surface and the inner side surface of the cryogenic vessel for holding the respective one of the magnetic sensors, the support base being fitted into the through hole of the pipe body.

10. The magnetic measuring apparatus according to claim 9, wherein the support base includes a first support base secured to the one of the inner bottom surface and the inner side surface of the cryogenic vessel and a second support base pivotably mounted to the first support base.

11. The magnetic measuring apparatus according to claim 10, wherein the guide lines are elastic tubes expandable and contractible in radial directions thereof so that the first ends of the guide lines are fitable over portions of the magnetic sensor holders.

12. The magnetic measuring apparatus according to claim 7 or 11 wherein each of the magnetic sensors has a pullup line with a first end connected to the magnetic sensor and a portion extendable out through the access opening of the cryogenic for removing the magnetic sensor connected thereto.

13. The magnetic measuring apparatus according to claim 12, wherein the magnetic sensors are each integrated with a pipe body and the connecting means includes the pipe body having a through hole through which the associated one of the guide lines is passed and the pipe body is joined to the first end of an associated one of the pullup lines.

14. The magnetic measuring apparatus according to claim 13, wherein the pipe bodies of the magnetic sensors are formed to be splitable when the associated one of the pullup lines is pulled to permit removal from the respective one of the magnetic sensor holders.

15. The magnetic measuring apparatus according to claim 7, wherein the one of the inner bottom surface and the inner side surface of the cryogenic vessel is the inner side surface and has two arrays of the magnetic sensor holders with the magnetic sensors installed thereon, said two arrays being disposed apart from one another for simultaneously performing measurements of two test objects situated within measurement range of the magnetic sensors installed on respective ones of said two arrays.

16. A magnetic measuring apparatus comprising:
 a cryogenic vessel having a top surface with an access opening and an inner surface;
 magnetic sensors installed in the cryogenic vessel;
 signal lines extending from the magnetic sensors through the access opening;
 a coolant filling the cryogenic vessel;
 a lid closing the access opening; and
 two arrays of magnetic sensor holders mounted on the inner surface of the cryogenic vessel and having respective ones of the magnetic sensors mounted thereon, said two arrays being disposed apart from one another for simultaneously performing measurements of two test objects situated respectively within measurement ranges of said magnetic sensors mounted on said two arrays.

17. The magnetic measuring apparatus according to claim 3, wherein the support base has a flexible guide member extending therefrom over which the pipe body is guided onto the support base.

18. The magnetic measuring apparatus according to claim 17, wherein the guide lines are elastic tubes expandable and contractible in radial directions thereof so that the first ends of the guide lines are fitable over the flexible guide member.

19. The magnetic measuring apparatus according to claim 9, wherein the support base has a flexible guide member extending therefrom over which the pipe body is guided onto the support base.

20. The magnetic measuring apparatus according to claim 19, wherein the guide lines are elastic tubes expandable and contractible in radial directions thereof so that the first ends of the guide lines are fitable over the flexible guide member.

21. A magnetic measuring apparatus comprising:
 a cryogenic vessel having a top surface with an access opening and an interior surface;
 a lid for closing said access opening;
 at least one array of magnetic sensor assemblies installed on said interior surface; and
 at least a portion of said magnetic sensor assemblies each including:
  a sensor mount fixed to said interior surface;
  a magnetic sensor module adapted to removably mount on said sensor mount;
  a sensor module guide extending from said sensor mount to said access opening; and
  said magnetic sensor module including a means for slidably mounting said magnetic sensor module on said sensor module guide to permit said sensor module to slide between a first position whereat said magnetic sensor module is mounted on said sensor mount and a second position at said access opening.

22. The magnetic measuring apparatus according to claim 21 wherein said at least one array of said magnetic sensor assemblies is installed on an array area of said interior surface greater than an area of a projection of said access opening onto said array area.

23. The magnetic measuring apparatus according to claim 21 wherein said magnetic sensor module defines a mounting aperture into which said sensor mount is fitted when said magnetic sensor module is mounted in said sensor mount.

24. The magnetic measuring apparatus according to claim 23 wherein said means for slidable mounting includes a through hole in said magnetic sensor module defining said mounting aperture and said sensor module guide being slidably disposed through said through hole.

25. The magnetic measuring apparatus according to claim 23 wherein said magnetic sensor module is splitable to permit widening of said mounting aperture for removal of said magnetic sensor module from said sensor mount.

26. The magnetic measuring apparatus according to claim 25 wherein said magnetic sensor module has a pull string device attached to opposing portions of said magnetic sensor module such that tension on said pull string device effects at least partial splitting of said magnetic sensor module.

27. The magnetic measuring apparatus according to claim 24, wherein said sensor module guide is an elastic tube expandable and contractible in radial directions thereof, and said elastic tube has a first end fitable over a portion of said sensor mount.

28. The magnetic measuring apparatus according to claim 24, wherein said sensor mount has a flexible guide member extending therefrom and fitable into said through hole of said sensor module to guide said sensor module onto said sensor mount.

29. The magnetic measuring apparatus according to claim 28, wherein said sensor module guide is an elastic tube expandable and contractible in radial directions thereof, and said elastic tube has a first end fitable over at least a portion of said flexible guide member.

30. The magnetic measuring apparatus according to claim 24, wherein the sensor mount includes a first support base secured to said inner surface of the cryogenic vessel and a second support base pivotably mounted to said first support base.

31. The magnetic measuring apparatus according to claim 30, wherein said sensor mount has a flexible guide member extending from said second support base and fitable into said through hole of said sensor module to guide said sensor module onto said sensor mount.

32. The magnetic measuring apparatus according to claim 31, wherein said sensor module guide is an elastic tube expandable and contractible in radial directions thereof, and said elastic tube has a first end fitable over at least a portion of said flexible guide member.

33. The magnetic measuring apparatus according to claim 21, wherein said sensor module guide is an elastic tube expandable and contractible in radial directions thereof, and said elastic tube has a first end fitable over a portion of said sensor mount.

34. The magnetic measuring apparatus according to claim 21, wherein said inner surface of the cryogenic vessel has two arrays of said magnetic sensor assemblies disposed apart from one another for performing measurements of respective ones of two test objects simultaneously.

35. A magnetic measuring apparatus comprising:
 a cryogenic vessel having a top surface with an access opening and an interior surface;
 a lid for closing said access opening;
 at least one array of magnetic sensor assemblies installed on said interior surface; and
 at least a portion of said magnetic sensor assemblies each including:
  a sensor mount fixed to said interior surface;
  a magnetic sensor module adapted to removably mount on said sensor mount;
  a sensor module guide extending from a position on said interior surface proximate said sensor mount to said access opening; and
  said magnetic sensor module including a means for slidably mounting said magnetic sensor module on said sensor module guide to permit said sensor module to slide between a first position whereat said magnetic sensor module is mounted on said sensor mount and a second position at said access opening.

36. The magnetic measuring apparatus according to claim 35 wherein said at least one array of said magnetic sensor assemblies is installed on an array area of said interior surface greater than an area of a projection of said access opening onto said array area.

37. The magnetic measuring apparatus according to claim 35 wherein said magnetic sensor module defines a mounting aperture into which said sensor mount is fitted when said magnetic sensor module is mounted in said sensor mount.

38. The magnetic measuring apparatus according to claim 37 wherein said means for slidably mounting includes said magnetic sensor module having a portion defining a through hole through which said sensor module guide is slidably disposed.

39. The magnetic measuring apparatus according to claim 35 wherein said means for slidably mounting includes said magnetic sensor module having a portion defining a through hole through which said sensor module guide is slidably disposed.

40. A magnetic measuring apparatus comprising:
 a cryogenic vessel having a top surface with an access opening, an exterior surface and an interior surface;
 a lid for closing said access opening;
 said cryogenic vessel having two concavities in said exterior surface defining corresponding convexities on said interior surface; and
 an array of magnetic sensor assemblies installed on said interior surface at each of said convexities for performing measurements of respective ones of two test objects situated at respective ones of said two concavities simultaneously.

41. A magnetic measuring apparatus comprising:
 a cryogenic vessel having a top surface with an access opening, an exterior surface and an interior surface:
 a lid for closing said access opening:
 said cryogenic vessel having two concavities in said exterior surface defining corresponding convexities on said interior surface:
 an array of magnetic sensor assemblies installed on said interior surface at each of said convexities for performing measurements of respective ones of two test objects situated at respective ones of said two concavities simultaneously; and
 at least a portion of said magnetic sensor assemblies each including:
  a sensor mount fixed to said interior surface;
  a magnetic sensor module adapted to removably mount on said sensor mount;
  a sensor module guide extending from said sensor mount to said access opening; and
  said magnetic sensor module including a means for slidably mounting said magnetic sensor module on said sensor module guide to permit said sensor module to slide between a first position whereat said magnetic sensor module is mounted on said sensor mount and a second position at said access opening.

* * * * *